United States Patent
Pfeifer et al.

(10) Patent No.: US 12,286,465 B2
(45) Date of Patent: Apr. 29, 2025

(54) CHIMERIC ANTIGEN RECEPTOR WITH A SPACER COMPRISING C2-SET IG-LIKE DOMAINS

(71) Applicant: Miltenyi Biotec B.V. & Co. KG, Bergisch Gladbach (DE)

(72) Inventors: Rita Pfeifer, Cologne (DE); Daniel Schäfer, Cologne (DE); Ian Johnston, Rosrath (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 1008 days.

(21) Appl. No.: 17/331,768

(22) Filed: May 27, 2021

(65) Prior Publication Data
US 2021/0371490 A1 Dec. 2, 2021

(30) Foreign Application Priority Data

May 28, 2020 (EP) .................................... 20177214

(51) Int. Cl.
| | | |
|---|---|---|
| C07K 14/705 | (2006.01) | |
| A61K 40/11 | (2025.01) | |
| A61K 40/31 | (2025.01) | |
| A61K 40/42 | (2025.01) | |
| C07K 14/47 | (2006.01) | |
| C07K 16/28 | (2006.01) | |
| A61K 38/00 | (2006.01) | |

(52) U.S. Cl.
CPC ............ *C07K 14/705* (2013.01); *A61K 40/11* (2025.01); *A61K 40/31* (2025.01); *A61K 40/4202* (2025.01); *A61K 40/4221* (2025.01); *A61K 40/4266* (2025.01); *C07K 16/28* (2013.01); *A61K 38/00* (2013.01); *A61K 2239/38* (2023.05); *A61K 2239/48* (2023.05); *A61K 2239/54* (2023.05); *C07K 14/4726* (2013.01); *C07K 2317/622* (2013.01); *C07K 2319/02* (2013.01); *C07K 2319/03* (2013.01); *C07K 2319/30* (2013.01)

(58) Field of Classification Search
CPC ................. C07K 14/705; C07K 16/28; C07K 2317/622; C07K 2319/30
See application file for complete search history.

(56) References Cited

U.S. PATENT DOCUMENTS

| | | | |
|---|---|---|---|
| 9,233,125 B2 | 1/2016 | Davila et al. | |
| 10,508,143 B1* | 12/2019 | Lobb | C07K 14/70503 |
| 11,254,726 B2* | 2/2022 | Kamb | A61K 39/4611 |
| 2019/0209611 A1* | 7/2019 | Eckardt | A61K 39/4611 |
| 2022/0211831 A1* | 7/2022 | Cohen | A61K 39/464412 |

FOREIGN PATENT DOCUMENTS

| | | |
|---|---|---|
| WO | WO 2012/082841 | 8/2012 |
| WO | WO 2013/044225 | 3/2013 |
| WO | WO 2014/127261 | 8/2014 |
| WO | WO 2015/075469 | 5/2015 |
| WO | WO 2015/075470 | 5/2015 |
| WO | WO 2015/142314 | 9/2015 |
| WO | WO 2016/030414 | 3/2016 |
| WO | WO 2016/055551 | 4/2016 |
| WO | WO 2016/097231 | 6/2016 |
| WO | WO 2016/193696 | 12/2016 |
| WO | WO 2017/058753 | 4/2017 |
| WO | WO 2017/064084 | 4/2017 |
| WO | WO 2017/068361 | 4/2017 |
| WO | WO 2017/091546 | 6/2017 |
| WO | WO 2018/061012 | 4/2018 |
| WO | WO 2019/162695 | 8/2019 |

OTHER PUBLICATIONS

Meril, Sara, et al. "Targeting glycosylated antigens on cancer cells using siglec-7/9-based CAR T-cells." Molecular Carcinogenesis 59.7 (2020): 713-723. (Year: 2020).*
Zah, Eugenia, et al. "T cells expressing CD19/CD20 bispecific chimeric antigen receptors prevent antigen escape by malignant B cells." Cancer immunology research 4.6 (2016): 498-508. (Year: 2016).*
Urbanska, Katarzyna, et al. "A universal strategy for adoptive immunotherapy of cancer through use of a novel T-cell antigen receptor." Cancer research 72.7 (2012): 1844-1852. (Year: 2012).*
Pronker, M. F., Lemstra, S., Snijder, J., Heck, A. J., Thies-Weesie, D. M., Pasterkamp, R. J., & Janssen, B. J. (2016). Structural basis of myelin-associated glycoprotein adhesion and signalling. Nature communications, 7(1), 13584. (Year: 2016).*
Bork et al., "The immunoglobulin fold: structural classification, sequence patterns and common core," Journal of Molecular Biology, Sep. 29, 1994, 242(4):309-20.
Garcia et al., "An αβ T cell receptor structure at 2.5 Å and its orientation in the TCR-MHC complex," Science, Oct. 11, 1996, 274(5285):209-19.
Gross et al., "Expression of immunoglobulin-T-cell receptor chimeric molecules as functional receptors with antibody-type specificity," Proceedings of the National Academy of Sciences, Dec. 1, 1989, 86(24):10024-8.
Huang et al., "Immunoglobulin superfamily proteins: structure, mechanisms, and drug discovery," Peptide Science, 1997, 43(5):367-82.
Hudecek et al., "Receptor affinity and extracellular domain modifications affect tumor recognition by ROR1-specific chimeric antigen receptor T cells," Clinical Cancer Research, Jun. 15, 2013, 19(12):3153-64.

(Continued)

*Primary Examiner* — Julie Wu
*Assistant Examiner* — Bryan William Heck
(74) *Attorney, Agent, or Firm* — Christian Biervert, Esq.; Fish & Richardson P.C.

(57) ABSTRACT

Provided herein are chimeric antigen receptors (CARs) that include a) an antigen binding domain specific for an antigen, b) a spacer, c) a transmembrane domain, and d) an intracellular signaling domain, wherein the spacer consists of 1, 2 or 3 C2-set Ig-like domain(s) e.g., C2-set Ig-like domains of the sialic acid binding Ig-like lectin (Siglec) family. Also provided herein are compositions including a) an immune cell expressing a CAR, wherein the CAR is specific for a tag and b) a tagged polypeptide.

12 Claims, 11 Drawing Sheets

Specification includes a Sequence Listing.

(56) References Cited

OTHER PUBLICATIONS

Hudecek et al., "The nonsignaling extracellular spacer domain of chimeric antigen receptors is decisive for in vivo antitumor activity," Cancer Immunology Research, Feb. 1, 2015, 3(2):125-35.
Krummel et al., "The immunological synapse: a dynamic platform for local signaling," Journal of Clinical Immunology, May 1, 2010, 30(3):364-72.
Natarajan et al., "Immunoglobulin Superfamily," Encyclopedia of Life, May 30, 2001, 6 pages.
Patel et al., "Impact of chimeric immune receptor extracellular protein domains on T cell function," Gene Therapy, Mar. 1999, 6(3):412-9.
Watanabe et al., "Fine-tuning the CAR spacer improves T-cell potency," Oncoimmunology, Dec. 1, 2016, 5(12):e1253656, 39 pages.
Extended European Search Report in European Appln. No. 21176238.0, mailed on Oct. 25, 2021, 8 pages.
Guedan et al., "Engineering and design of chimeric antigen receptors," Molecular Therapy—Methods & Clinical Development, Mar. 2019, 12:145-156.
Läubli et al., "Sialic acid-binding immunoglobulin-like lectins (Siglecs) detect self-associated molecular patterns to regulate immune responses," Cellular and Molecular Life Sciences, Feb. 2020, 77(4):593-605.
Lipowska-Bhalla et al., "Targeted immunotherapy of cancer with CAR T cells: achievements and challenges," Cancer Immunology, Immunotherapy, Jul. 2012, 61:953-962.
Schäfer et al., "A novel Siglec-4 derived spacer improves the functionality of CAR T cells against membrane-proximal epitopes," Frontiers in Immunology, Aug. 2020, 11:1704, 18 pages.

\* cited by examiner

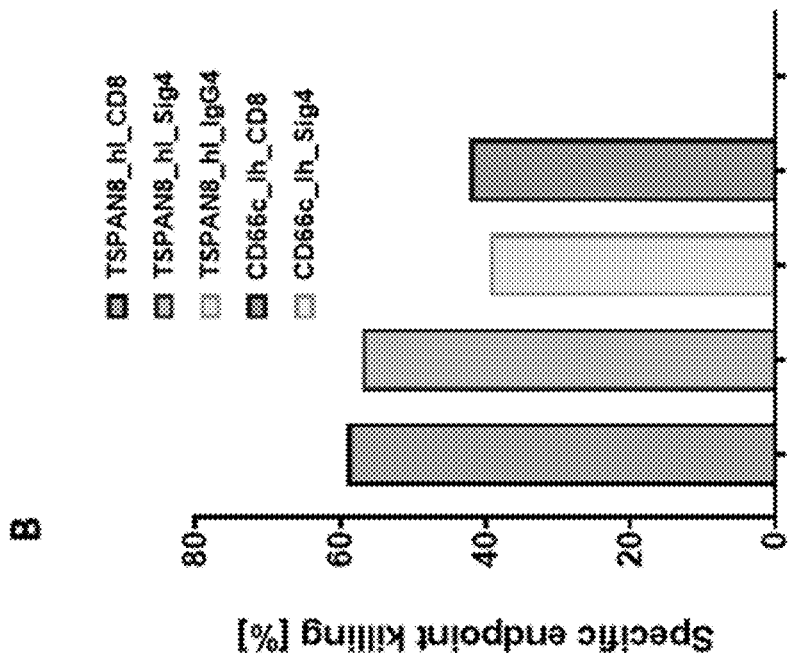
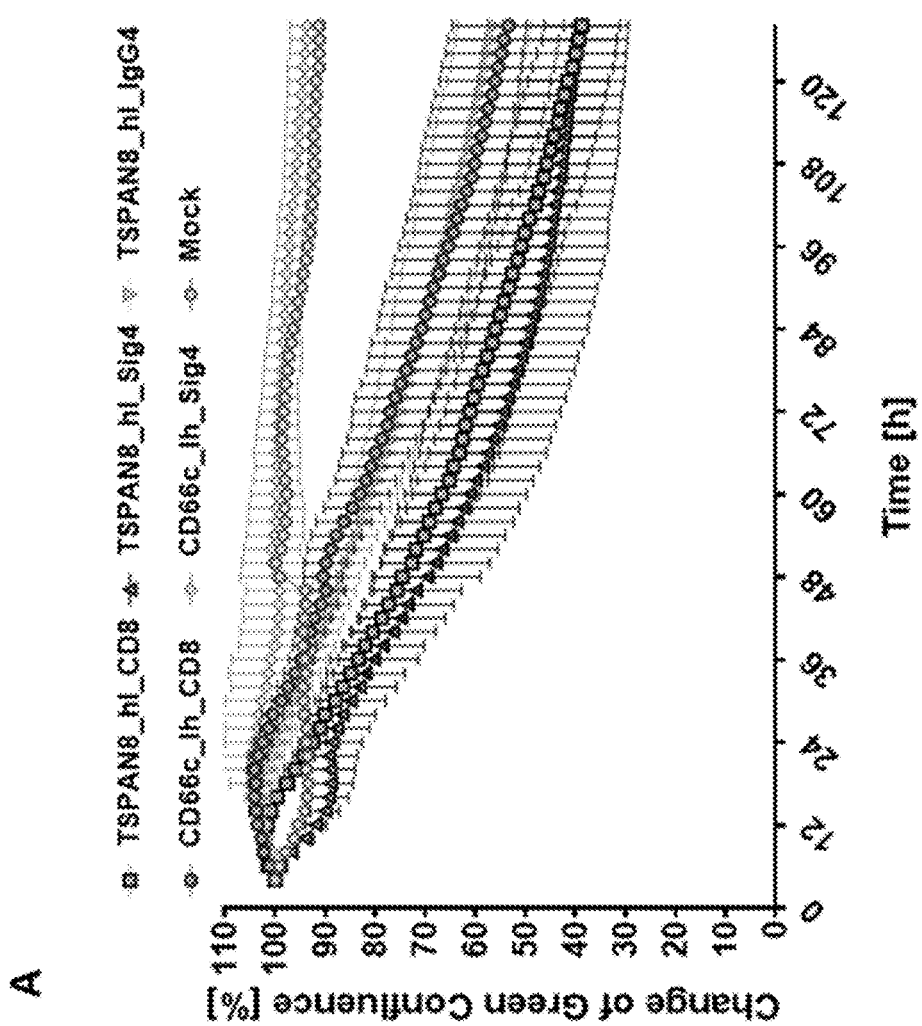
FIG. 4B
FIG. 4A

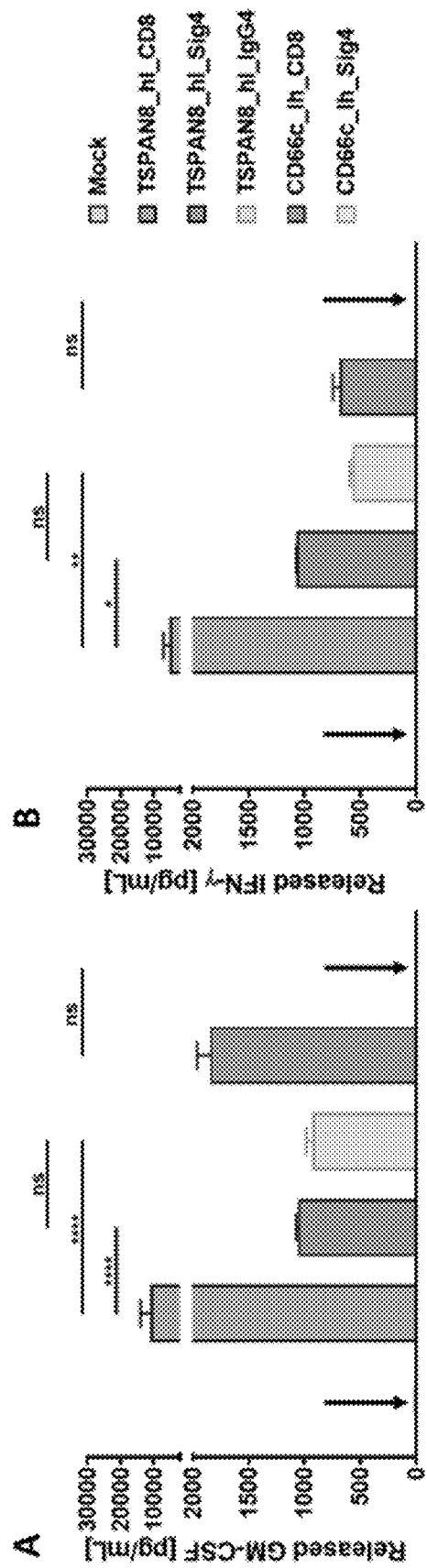
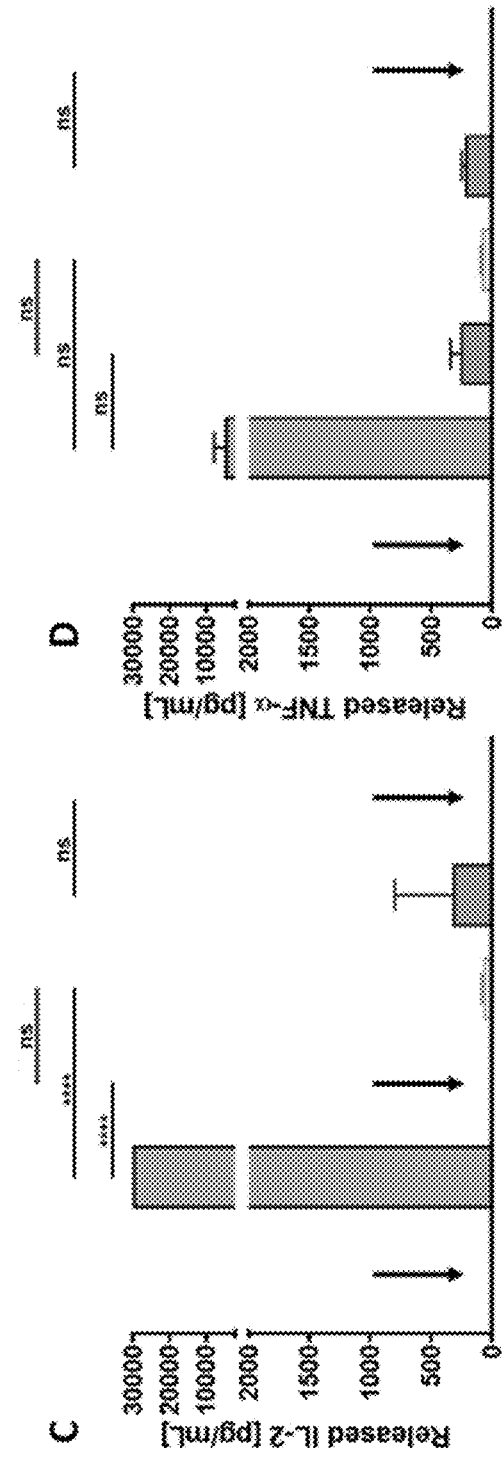
FIG. 6A
FIG. 6B
FIG. 6C
FIG. 6D

CHIMERIC ANTIGEN RECEPTOR WITH A SPACER COMPRISING C2-SET IG-LIKE DOMAINS

CROSS-REFERENCE TO RELATED APPLICATIONS

This application claims the benefit of European Patent Application No. EP 20177214.2, filed on May 28, 2020, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Apr. 28, 2021, is named Sequence_Listing.txt and is 44.5 kilobytes in size.

FIELD OF THE INVENTION

The present invention relates to the field of chimeric antigen receptors (CARs) having a spacer between antigen binding domain and transmembrane domain, in particular having a spacer that comprises at least one C2-set Ig-like domain.

BACKGROUND

While CAR therapies have now achieved public recognition, their development and the quest for optimal CAR design has been a multistep process. Ever since their initial description in 1989 by Eshhar and colleagues (Gross et al., 1989), the receptors have evolved from a two-chimeric-TCR chain architecture to a one-protein design which commonly incorporates a single-chain variable fragment (scFv) of a given antibody as the antigen binding moiety, an extracellular spacer and a transmembrane region as structural features, as well as signal transduction units for T cell activation. Originally, the spacer domain was introduced into the CAR framework as an inert building block to allow the antigen binding moiety to extend beyond the T cell's glycocalyx and improve antigen accessibility. Following this assumption, a plethora of spacer regions was designed simultaneously ranging from the immunoglobulin (Ig) domains of the crystallizable fragments (Fc) of antibodies to extracellular domains of CD8α, CD28, the TCRβ chain or NKG2D and were applied without comparative analyses. However, already very early on, Patel and colleagues provided the scientific proof that the spacer region can be of paramount importance for the receptor function and affects its expression, surface stability, and signal transduction (Patel et al., 1999). More recent accumulating research has further been showing that in addition to the nature of the spacer, effective antigen recognition depends on the functional interplay between the spatial localization of the target epitope and the CAR spacer length.

The use of Ig-derived spacers is particularly attractive as it provides the opportunity to modulate the spacer length into long (CH2-CH3 domain), medium (CH3) and short (hinge only) structures, while retaining the nature of the parent protein. However, Ig-derived spacers have faced various complications during their development. In particular, off-target activation, CAR T cell sequestration in the lung, tonic signaling and activation-induced cell death (AICD) have been described leading to only a limited T cell persistence (Hudecek et al., 2015; Watanabe et al., 2016). Although these effects could be abrogated by mutating the amino acid sequence essential for FcR binding, it needs to be taken into consideration that these experiments were conducted in immunosuppressed NSG mice and whether FcR binding can be completely eliminated in humans remains unclear. Of note, several clinical studies that used IgG-derived spacers described only limited anti-tumor efficacy and low CAR T cell persistence. In fact, the only currently approved CAR T cell-based therapies use CD28 (Yescarta) and CD8 (Kymriah) as spacer domains. In addition, a severe side effect that may occur during CAR T cell therapy with state-of-the-art CARs is the cytokine release syndrome (CRS). CRS can complicate treatment of patients and can be a restricting dosing factor, as it is correlated with the number of injected CART cells. In worst case, CRS can have a fatal outcome for the patient.

There is a need in the art for an improved or alternative CAR construct which, when expressed in an immune cell, demonstrates lower off-target activation and/or reduces the chances for CRS.

SUMMARY OF THE INVENTION

Surprisingly it was found that a CAR comprising a spacer that preferentially comprises 1 to 3 C2-set Ig-like domains reduces the off-target activation in vitro and in vivo, when expressed in an immune cell and compared to other state-of-the-art CARs. Said spacer shifted phenotypes of said immune cell to a greater extent into a memory phenotype during in vivo expansion with lower exhaustion marker upregulation and lower cytokine release in vitro, while exhibiting the same or better cytotoxicity as compared to other state-of-the-art CARs. Said spacer may comprise a C2-set Ig-like domain of the sialic acid binding Ig-like lectin (Siglec) family. Said spacer may comprise no C1-set Ig-like domain.

BRIEF DESCRIPTION OF THE DRAWINGS

(FIG. 1A) Modular structure of the CD20 CAR constructs with the C2-set Ig-like domain spacers and extracellular domain comparison of the CAR constructs. (FIG. 1B) Schematic of CD20 specific C2-set Ig-like domain spacer CARS compared to CD8a spacer CAR.

(FIGS. 2A-B) Expression analysis of the CAR constructs in transiently transfected HEK293T cells 24 h post transfection (FIG. 2A) and in transduced T cells (FIG. 2B) from two donors 6 days post transduction. LNGFR and CAR expression were evaluated by flow cytometry. (FIGS. 2C-E) C2-set Ig-like domain spacer CAR T cells were cocultured with Raji or HEK293T cells for 5 h at a ratio of 1:1 and T cell expression of CD107a (FIG. 2C) and intracellular TNF-α (FIG. 2D) were analyzed by flow cytometry. (FIG. 2E) The frequency of TIM3, LAG3 and PD1 triple positive CART cells was analyzed after 24 h co-culture at a 1:2 ratio of CART cells to Raji or HEK293T cells by flow cytometry. CAR T cells alone were also cultured in order to exclude tonic signaling/unspecific activation. n=3. Error bars, mean±SD. ns>0.05, *p<0.05, p<0.01, *p<0.001 and ****p<0.0001 [one-way ANOVA, CAR T+Raji compared to Untreated (UnTd)].

(FIG. 3A) Modular structure of the CD66c and TSPAN8 CAR constructs with the C2-set Ig-like domain spacers and extracellular domain comparison of the CAR constructs. (FIG. 3B) Schematic of CD66c and TSPAN8 specific C2-set Ig-like domain spacer CARs compared to CD8a and IgG4 CH2-CH3 spacer CAR.

FIGS. 4A and 4B depict dynamic monitoring of in vitro cytotoxicity mediated by T cells expressing different spacer CAR constructs directed against TSPAN8 or CD66c. (FIG. 4A) On day 11 after T cell transduction, AsPC1 target cells stably expressing eGFP were co-cultured with different CAR T cell groups at an effector to target cell ratio of 2:1 and fluorescence emission was measured in the IncuCyte® imaging platform for 132 hours with 2 hours interval. Co-cultures with untransduced T cells served as negative control. Shown is one representative from 2 separate experiments and 6 donors in total. (FIG. 4B) After 132 hours of co-culture (endpoint), the total killing efficacy was determined compared to the control group.

FIGS. 6A-D depict cytokine secretion by CAR-transduced T cells following antigen stimulation. On day 11 following transduction, TSPAN8 and CD66c CAR T cells incorporating different spacer domains were co-cultured with the target cell line AsPC1 at an effector to target cell ratio of 1:2 for 24 hours and culture supernatants were analyzed for cytokine release using the MACSPlex technique. Cultures of non-modified T cell with target cells served to assess the specificity of CAR-mediated lymphocyte response. Secretion pattern for (FIG. 6A) GM-CSF, (FIG. 6B) IFNγ, (FIG. 6C) IL-2, and (FIG. 6D) TNFα is shown. Data is representative for n=2. Shown is the mean±SD. ns>0.05, *p<0.05, p<0.01, *p<0.001 and ****p<0.0001 [one-way ANOVA, multiple comparisons].

(FIG. 8A) Tumor burden and change in tumor size over time after TSPAN8 CAR T cell infusion. Untreated and Mock T cell treated animals served as controls, T cells from one donor were used. IgG4: n=5; Sig4 and CD8a: n=4. PSM p<0.05 (significant) [one-way ANOVA, multiple comparisons]. Organization of the pairwise significant matrix for group comparison of in vivo performance of TSPAN8_hl_CD8, TSPAN8_hl_Sig4, TSPAN8_hl_IgG4, Untreated and Mock. PSM p<0.05 [one-way ANOVA, multiple comparisons]. (FIG. 8B) Total number of CAR positive T cells recovered from spleens of TSPAN8 CAR-treated animals at the end of the experiment calculated after flow cytometric analysis. IgG4: n=5; Sig4 and CD8α: n=4.

Figures 1A, 1B:
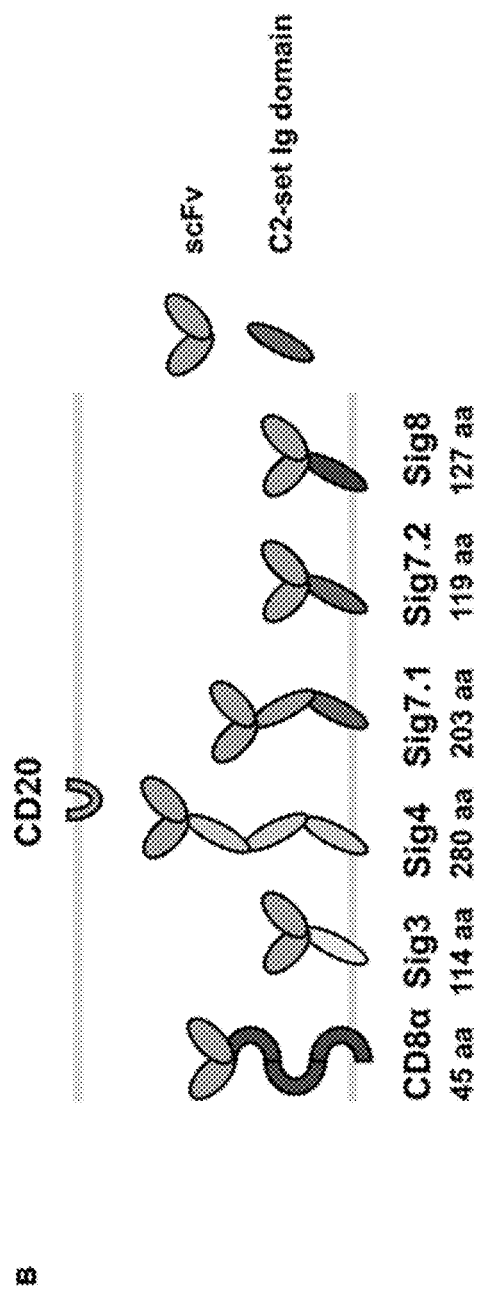
FIGS. 1A and 1B depict the design of C2-set Ig-like domain containing CARs specific for CD20.

Ig-like domains are classified according to the number of β-strands into 4 different groups called "sets": C1-set domains are classical Ig-like domains and are composed of β-sheet I constituted by the β-strands A, B, D, and E and β-sheet II formed by the β-strands C, F, and G. Such C1-set domains are found exclusively in molecules involved in the immune system. In C2-set domains, the β-strand D is deleted and replaced by the β-strand C' which is directly connected to β-strand E. In this fold, sheet I is composed of the β-strands A, B, E and sheet II of the β-strands C', C, F and G. The group designated as V-set domain contain the two additional β-strands C' and C" between β-strand C and D and sheet I is formed by the β-strands A, B, E, and D, whereas sheet II is composed of the β-strands C", C', C, F, and G. The I-set domain can be described as a truncated V-set domain which is truncated on sheet II resulting in a missing C" strand. A hallmark of the V- and I-set domain is the A-A' kink in the N-terminal A β-strand.

DETAILED DESCRIPTION OF THE INVENTION

In a first aspect the present invention provides a CAR comprising
a) an antigen binding domain specific for an antigen
b) a spacer
c) a transmembrane domain
d) an intracellular signaling domain,
wherein said spacer may comprise at least one C2-set Ig-like domain.

Said CAR, wherein said spacer may comprise at least one C2-set Ig-like domain, and wherein said spacer does not comprise a C1-set Ig-like domain.

The spacer of a CAR may be the peptidic linkage between the extracellular antigen binding domain of a CAR and the transmembrane domain of a CAR.

Said C2-set Ig-like domain is characterized by seven antiparallel beta-strands, presented in two beta-sheets of three (ABE) and four (CC'FG) strands.

Said C1-set Ig-like domain is characterized by eight antiparallel beta-strands, presented in two beta-sheets of four (ABED) and four (CC'FG) strands.

The C1-set Ig-like domain and the C2-set Ig-like domain are also defined in more detail below.

Said antigen binding domain may be antibody or antigen binding fragment thereof such as a svFc or a Fab.

Alternatively said antigen binding domain may be ligand such as a cytokine that can bind to the cognitive receptor present on a target cell or may be an antigen that may be able to bind to an antigen-specific B cell.

Said antigen may be an antigen expressed on the surface of a target cell such as a cancer cell. Said antigen may be a soluble antigen, e.g. a soluble antigen that may be coupled to a solid surface or matrix such as a bead, or a soluble antigen that may allow for cross-linking, i.e. that induces dimerization of the CAR.

Said antigen may be a tagged polypeptide as disclosed herein. Then the antigen binding domain of said CAR may be specific for the tag, and the polypeptide may be bind to a antigen expressed on the surface of a target cell.

Said intracellular (cytoplasmic) signaling domain may comprise at least one primary cytoplasmic signaling domain comprising an immunoreceptor tyrosine-based activation motif (ITAM) and/or at least one co-stimulatory signaling domain.

Said primary cytoplasmic signaling domain of said first CAR may be CD3zeta.

Said at least one co-stimulatory domain of said first CAR, may be selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB, and CD28.

Said intracellular (cytoplasmic) signaling domain may comprise at least one inhibitory endodomain, wherein said at least one inhibitory endodomain is a cytoplasmic signaling domain comprising at least one signal transduction element that inhibits an immune cell or comprising at least one element that induces apoptosis.

In one embodiment of the invention the CAR as disclosed herein may comprise a spacer comprising or consisting of 1, 2 or 3 C2-set Ig-like domain(s).

In one embodiment of the invention the CAR as disclosed herein may comprise a spacer comprising 1, 2 or 3 C2-set Ig-like domain(s) and no C1-set Ig-like domain.

In one embodiment of the invention the CAR as disclosed herein may be a CAR, wherein said antigen binding domain and said spacer are from different proteins.

In one embodiment of the invention the CAR as disclosed herein may be a CAR, wherein said C2-set Ig-like domain(s) is/are selected from the group of C2-set Ig-like domains of the sialic acid binding Ig-like lectin (Siglec) family.

In one embodiment of the invention the CAR as disclosed herein may be a CAR, wherein said Siglec family may comprise Siglec-1, Siglec-2, Siglec-3, Siglec-4, Siglec-5, Siglec-6, Siglec-7, Siglec-8, Siglec-9, Siglec-10, Siglec-11, Siglec-12, Siglec-13, Siglec-14, Siglec-15, Siglec-16 and Siglec-17.

In a preferred embodiment of the invention the CAR as disclosed herein may be a CAR, wherein said C2-set Ig-like domain(s) is/are selected from the C2-set Ig-like domain(s) of Siglec-4, Siglec-7 and Siglec-8.

In one embodiment of the invention the CAR as disclosed herein may be a CAR, wherein said spacer may comprise or may consist of SEQ ID NO:1 or SEQ ID NO:2 or SEQ ID NO:3 or SEQ ID NO:4.

In one embodiment of the invention the CAR as disclosed herein may be a CAR, wherein said antigen binding domain may be specific for CD20.

In one embodiment of the invention the CAR as disclosed herein may be a CAR, wherein said antigen binding domain may be specific for CD20, wherein said antigen binding domain may comprise the SEQ ID NO:5.

In one embodiment of the invention the CAR as disclosed herein may be a CAR comprising SEQ ID NO:6 or SEQ ID NO:7 or SEQ ID NO:8 or SEQ ID NO:9.

In one embodiment of the invention the CAR as disclosed herein may be a CAR, wherein said antigen binding domain may be specific for TSPAN8.

In one embodiment of the invention the CAR as disclosed herein may be a CAR, wherein said antigen binding domain may be specific for TSPAN8, wherein said antigen binding domain may comprise the SEQ ID NO:10.

In one embodiment of the invention the CAR as disclosed herein may be a CAR comprising SEQ ID NO:11.

T cell activation requires interactions between a TCR and an antigen presenting molecule such as MHC1, presenting an antigen-specific peptide. The binding of these two molecules occurs at a specialized cell-cell junction called an immunological synapse (or immune synapse) which is the interface between an antigen-presenting cell or target cell and a lymphocyte such as a T cell or Natural Killer cell. This synapse comprises at least 2 domains: a central cluster of engaged antigen-specific receptors surrounded by a second domain populated with adhesion molecules.

Figure 2A:
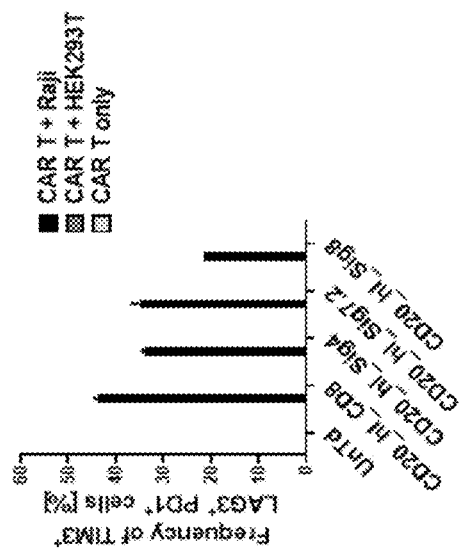
FIGS. 2A-E depict in vitro evaluation of novel C2-set Ig-like domain CD20 specific Siglec spacer CAR T cells.
Figure 2B:
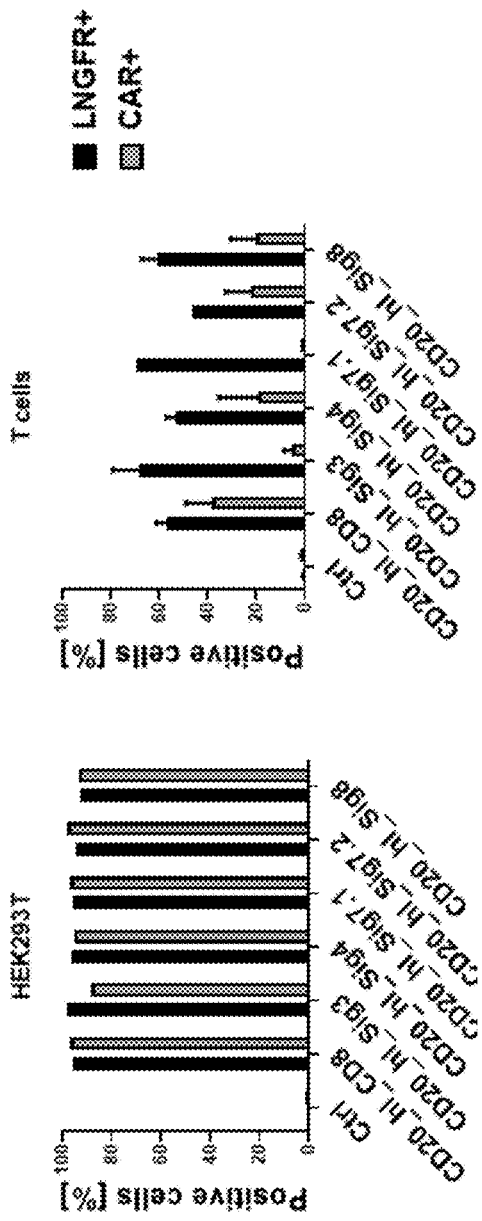
Figure 2C:
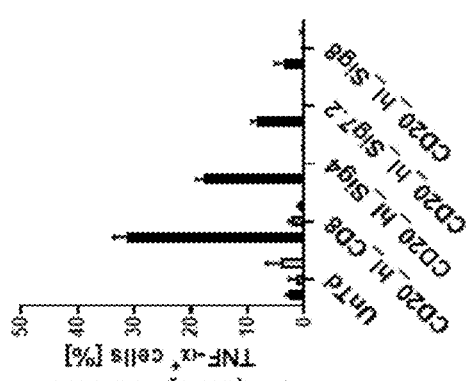
Figure 2D:
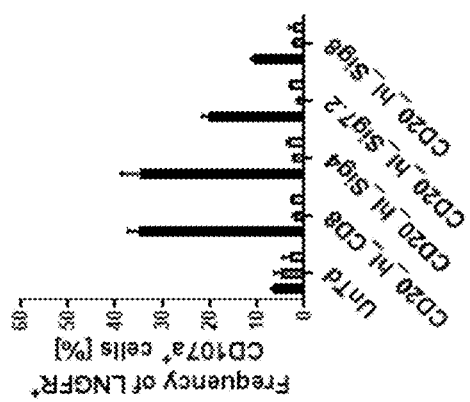
Figure 2E:
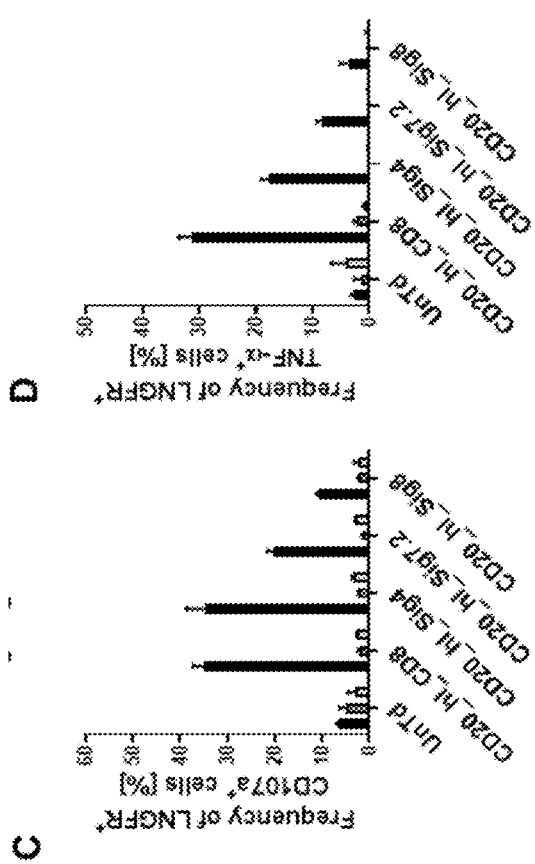

When TCR and MHC1 are engaged, the spacing at their point of interaction is 15 nm (Garcia et al, 1996). Microscopical analysis of T cells interacting with antigen presenting cells shows a dynamic structure with nodes of tighter interaction being interspersed with areas where the membrane spacing approaches 100 nm (Krummel and Cahalan 2010). However, the parts with larger spacing will allow other molecules to interact (e.g. adhesion molecules, glycocalyx spacing) and not the TCR with the peptide-MHC complex which is strictly limited to about 15 nm. But there is evidence that the immunological synapse tolerates a certain flexibility with regard to the spacing of a CAR-antigen interaction leading to a functional spacing also when the distance is about 20 nm or even larger. In Hudecek et al (2013) it is shown that both a CAR comprising a hinge alone and a CAR comprising a CH2 spacer which differ in length by approximately 3.5 nm can kill target cells in vitro. Herein it is also shown in FIGS. 2C-E that the CD20 CAR is also functional with a spacer comprising one C2-set Ig-like domain or three C2-set Ig-like domains (CD20_hl_Sig7.2 vs. CD20_hl_Sig4) which differ by approximately 7 nm in length.

Said CAR, wherein said antigen binding domain is specific for an epitope on an antigen expressed on a cell membrane of a target cell, Wherein the total distance of the complex of spacer-antigen binding domain that has bound thereto said antigen via said epitope to said cell membrane of said target cell is according to the formula:

$$20 \text{ nm} \geq S + A1 + A2 \geq 7 \text{ nm, preferentially } 17 \text{ nm} \geq S + A1 + A2 \geq 7 \text{ nm, more preferentially } 15 \text{ nm} \geq S + A1 + A2 \geq 7 \text{ nm,}$$

wherein S is length of spacer in nm, wherein one C2-set domain is about 3.5 nm in size, Wherein A1 is the length in nm of antigen binding domain and wherein A2 is the distance in nm of the epitope of said antigen from the cell membrane of said target cell.

The total distance of the complex of spacer-antigen binding domain that has bound thereto said antigen via said epitope to said cell membrane of said target cell is equal to the distance between an immune cell and a target cell required to induce functional changes in said immune cell (to form an immunological synapse).

Normally, the length of an antigen binding domain is about 2 nm (between 2 to 4 nm) for a scFv and about 7 nm for a Fab and diabody.

The following embodiments exemplarily demonstrate the use of the formula.

In one embodiment said CAR may be a CAR specific for CD20 comprising three C2-set Ig-like domains, wherein the antigen binding domain is a scFv, wherein A1=2 nm, wherein A2=2.5 nm, wherein S=10.5 nm.

As the antigen CD20 is a proximal antigen it may be calculated that the distance in nm of the epitope of said antigen from the cell membrane of said target cell may be about 2.5 nm.

In one embodiment said CAR may be a CAR specific for CD20 comprising two C2-set Ig-like domains, wherein the antigen binding domain is a Fab, wherein A1=7 nm, wherein A2=2.5 nm, wherein S=7 nm.

Said CAR, wherein said antigen binding domain is specific for an epitope on an antigen expressed on a cell membrane of a target cell, wherein said epitope is a relatively proximal epitope, and wherein said spacer comprise two or three C2-set Ig-like domain, and wherein said spacer does not comprise a C1-set Ig-like domain.

Said CAR, wherein said antigen binding domain is specific for an epitope on an antigen expressed on a cell membrane of a target cell, wherein said epitope is a relatively distal epitope, and wherein said spacer comprise one or two C2-set Ig-like domain, and wherein said spacer does not comprise a C1-set Ig-like domain.

Said CAR, wherein said antigen binding domain is specific for an epitope on an antigen expressed on a cell membrane of a target cell, wherein said spacer comprises 1, 2 or 3 C2-set Ig-like domain(s) in dependence of the relatively distal or relatively proximal position of said epitope, and wherein said spacer does not comprise a C1-set Ig-like domain.

The terms "relatively distal" and "relatively proximal" may be used to indicate that there is a significant difference in the relative distance of the two epitopes, when directly compared, from the target cell membrane, significant enough to affect the optimal length of the spacers of the CAR as disclosed herein for optimal functionality of the CAR. The length of the spacer may dependent on the relative position of said epitope, the more distal the epitope the shorter is the spacer of the CAR, the more proximal the epitope the longer is the spacer of the CAR. As described above, the skilled person is aware of the spatial situation of an immunological synapse and would select the suited length of the spacer in dependence of the position of the epitope on the antigen expressed on a cell membrane of a target cell without inventive skills.

Said CAR, wherein the length of the spacer is such that the distance between the cell membranes of the target cell that expresses said antigen and the engineered immune cell that expresses said CAR creates an immune synapse, wherein said spacer does not comprise a C1-set Ig-like domain.

In another aspect the present invention provides a nucleic acid encoding a CAR comprising
a) an antigen binding domain specific for an antigen
b) a spacer
c) a transmembrane domain
d) an intracellular signaling domain,
wherein said spacer comprises at least one C2-set Ig-like domain.

In another aspect, the present invention provides an immune cell comprising a CAR comprising
a) an antigen binding domain specific for an antigen
b) a spacer
c) a transmembrane domain
d) an intracellular signaling domain,
wherein said spacer comprises at least one C2-set Ig-like domain.

Said immune cell may be a T cell or a NK cell.

In another aspect the present invention provides an immune cell comprising a nucleic acid encoding a CAR comprising
a) an antigen binding domain specific for an antigen
b) a spacer
c) a transmembrane domain
d) an intracellular signaling domain,
wherein said spacer comprises at least one C2-set Ig-like domain.

In another aspect the present invention provides a pharmaceutical composition comprising immune cells expressing a CAR comprising
a) an antigen binding domain specific for an antigen
b) a spacer
c) a transmembrane domain
d) an intracellular signaling domain,
wherein said spacer comprises at least one C2-set Ig-like domain,
and optionally a pharmaceutical acceptable carrier.

In one aspect the present invention provides a method for treating a subject suffering from a disease triggered by a target cell, the method comprising administering to said subject an immune cell expressing a CAR comprising
a) an antigen binding domain specific for an antigen expressed on the surface of said target cell
b) a spacer
c) a transmembrane domain
d) an intracellular signaling domain,
wherein said spacer comprises at least one C2-set Ig-like domain.

Said disease may be cancer and said target cell may be a cancer cell.

In one embodiment of the invention the immune cells expressing the CAR as disclosed herein are for use in treatment of a disease associated with a target cell of a subject suffering from said disease, the disease may be e.g. cancer and the target cell a cancerous cell. Immune cells, e.g. T cells or NK cells of a subject may be isolated. The subject may e.g. suffer from said cancer or may be a healthy subject. These cells are genetically modified in vitro or in vivo to express. The CAR as disclosed herein. These engineered cells may be activated and expanded in vitro or in vivo. In a cellular therapy these engineered cells are infused to a recipient in need thereof. These cells may be a pharmaceutical composition (said cell plus pharmaceutical acceptable carrier). The infused cells may be e.g. able to kill (or at least stop growth of) cancerous cells in the recipient. The recipient may be the same subject from which the cells was obtained (autologous cell therapy) or may be from another subject of the same species.

The immune cells, preferentially T cells or NK cells engineered to express the CAR as disclosed herein may be administered either alone, or as a pharmaceutical composition in combination with diluents and/or with other components such as IL-2 or other cytokines or cell populations. Briefly, pharmaceutical compositions of the present invention may comprise a cell population of genetically modified cells (a plurality of immune cells) as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Preferentially, the compositions of the present invention are formulated for intravenous administration. The administration of cell compositions to the subject may be carried out in any convenient manner known in the art.

Pharmaceutical compositions of the present invention may be administered in a manner appropriate to the disease to be treated. Appropriate dosages may be determined by clinical trials. But the quantity and frequency of administration will also be determined and influenced by such factors as the condition of the patient, and the type and severity of the patient's disease.

A pharmaceutical composition comprising the immune cells, preferentially T cells or NK cells as disclosed herein may be administered at a dosage of $10^4$ to $10^9$ cells/kg body weight, preferably $10^5$ to $10^6$ cells/kg body weight. The cell compositions may also be administered several times at these dosages. The compositions of cells may be injected e.g. directly into a tumor, lymph node, or site of infection.

The genetically engineered immune cells may be activated and expanded to therapeutic effective amounts using methods known in the art.

The immune cells of the invention may be used in combination with e.g. chemotherapy, radiation, immunosuppressive agents, antibodies or antibody therapies.

"Universal" CAR systems (or adapter CAR systems) that indirectly bind to target cells via soluble factors are described in the art. E.g. in WO2012082841A2, WO2013044225A1 and WO2016030414A1 tagged antibodies and tag-specific CAR are disclosed, wherein the tag may be either artificial (such as FITC) and potentially immunogenic or an endogenous molecule which may compete with the natural counterparts to the CAR binding.

Therefore, in another aspect the present invention provides a composition comprising
i) an immune cell comprising a CAR comprising
   a) an antigen binding domain specific for a tag of a tagged polypeptide
   b) a spacer
   c) a transmembrane domain
   d) an intracellular signaling domain,
   wherein said spacer comprises at least one C2-set Ig-like domain,
ii) said tagged polypeptide, wherein said polypeptide binds specifically to an antigen.

Said composition as disclosed herein, wherein said tagged polypeptide may be an antibody or antigen binding fragment thereof.

Said composition as disclosed herein, wherein said tag of said tagged polypeptide may be a hapten.

Said tagged polypeptide may comprise SEQ ID NO:5 or SEQ ID NO:10.

Said tag may be selected from the group consisting of dextran, biotin, fluorescein isothiocyanate (FITC), phycoerythrin (PE), peptides such as c-Myc-tag, Strep-Tag, Flag-Tag, Polyhistidine-tag or proteins such as streptavidin. Preferentially, the tag may be biotin or a derivate thereof.

All definitions, characteristics and embodiments defined herein with regard to the first aspect of the invention as disclosed herein also apply mutatis mutandis in the context of the other aspects of the invention as disclosed herein.

Definitions

Unless defined otherwise, technical and scientific terms used herein have the same meaning as commonly understood by one of ordinary skill in the art to which this invention belongs. As used herein the term "comprising" or "comprises" is used in reference to compositions, methods, and respective component(s) thereof, that are essential to the method or composition, yet open to the inclusion of unspecified elements, whether essential or not.

In general, a CAR may comprise an extracellular domain (extracellular part) comprising the antigen binding domain, a transmembrane domain and a cytoplasmic signaling domain (intracellular signaling domain). The antigen binding domain may be linked to the transmembrane domain by a spacer. The extracellular domain may also comprise a signal peptide. In some embodiments of the invention the antigen binding domain of a CAR binds a tag or hapten that is coupled to a polypeptide ("haptenylated" or "tagged" polypeptide), wherein the polypeptide may bind to a disease-associated antigen such as a tumor associated antigen (TAA) that may be expressed on the surface of a cancer cell.

Such a CAR may be referred to as "anti-tag" CAR or "adapterCAR" or "universal CAR" as disclosed e.g. in U.S. Pat. No. 9,233,125B2.

The haptens or tags may be coupled directly or indirectly to a polypeptide (the tagged polypeptide), wherein the polypeptide may bind to said disease associated antigen expressed on the (cell) surface of a target. The tag may be e.g. dextran or a hapten such as biotin or fluorescein isothiocyanate (FITC) or phycoerythrin (PE), but the tag may also be a peptide sequence e.g. chemically or recombinantly coupled to the polypeptide part of the tagged polypeptide. The tag may also be streptavidin. The tag portion of the tagged polypeptide is only constrained by being a molecular that can be recognized and specifically bound by the antigen binding domain specific for the tag of the CAR. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv.

A "signal peptide" refers to a peptide sequence that directs the transport and localization of the protein within a cell, e.g. to a certain cell organelle (such as the endoplasmic reticulum) and/or the cell surface.

Generally, an "antigen binding domain" refers to the region of the CAR that specifically binds to an antigen, e.g. to a tumor associated antigen (TAA) or tumor specific antigen (TSA). The CARs of the invention may comprise one or more antigen binding domains (e.g. a tandem CAR). Generally, the targeting regions on the CAR are extracellular. The antigen binding domain may comprise an antibody or an antigen binding fragment thereof. The antigen binding domain may comprise, for example, full length heavy chain, Fab fragments, single chain FAT (scFv) fragments, divalent single chain antibodies or diabodies. Any molecule that binds specifically to a given antigen such as affibodies or ligand binding domains from naturally occurring receptors may be used as an antigen binding domain. Often the antigen binding domain is a scFv. Normally, in a scFv the variable regions of an immunoglobulin heavy chain and light chain are fused by a flexible linker to form a scFv. Such a linker may be for example the "$(G4/S)_3$-linker".

In some instances, it is beneficial for the antigen binding domain to be derived from the same species in which the CAR will be used in. For example, when it is planned to use it therapeutically in humans, it may be beneficial for the antigen binding domain of the CAR to comprise a human or humanized antibody or antigen binding fragment thereof. Human or humanized antibodies or antigen binding fragments thereof can be made by a variety of methods well known in the art.

"Spacer" or "hinge" as used herein refers to the hydrophilic region which is between the antigen binding domain and the transmembrane domain. The CARs of the invention comprise an extracellular spacer as disclosed herein, i.e. it comprises at least one C2-set Ig-like domain, preferentially 1-3 C2-set Ig-like domains, and preferentially wherein said spacer does not comprise a C1-set Ig-like domain. This is in contrast to regularly used spacer of the art, where the spacer may include e.g. Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge.

Figure 10:
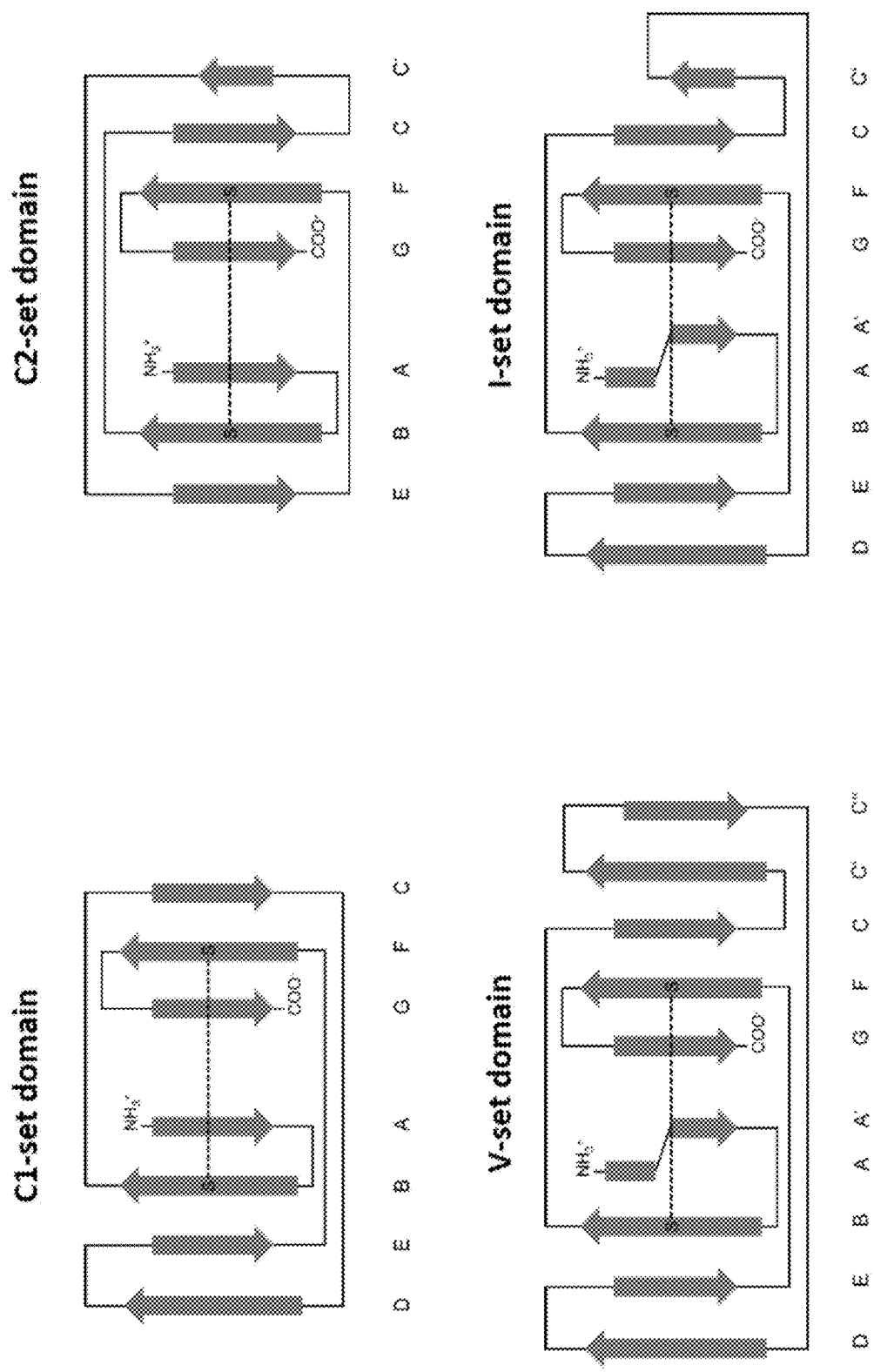
FIG. 10 shows that Ig-like domains are protein domains that are similar in amino acid sequence and structure to the Ig-domains of antibodies. Structurally, the immunoglobulin domain is composed of 7 to 10 β-strands that are arranged as two anti-parallel β-sheets packed tightly against each other forming a β-barrel. The two sheets are linked together by a conserved intradomain disulfide bond. The loops connecting the β-strands display a varying length and character and may form regular reverse turns or short α-helical structures, but in most cases are irregular.

A C2-set Ig-like domain is Ig-like domain that is characterized by seven antiparallel beta-strands, presented in two beta-sheets of three (ABE) and four (CC'FG) strands (FIG. 10).

A C1-set Ig-like domain is Ig-like domain that is characterized by eight antiparallel beta-strands, presented in two beta-sheets of four (ABED) and four (CC'FG) strands (FIG. 10).

The immunoglobulin superfamily (IgSF) is a large group of soluble and cell surface proteins that share a common structural feature, that was originally described in antibodies: the Ig fold. The overall shape of the domain can be described as a flattened cylinder or a-barrel. The basic folding motif consists of two layers of β-sheets with antiparallel β-strands that are stabilized by hydrophobic interactions and a central disulfide bond between two opposing strands. A β-sheet is commonly composed of 3-5 antiparallel β-strands, and 5-10 amino acids usually make up one β-strand. The strands are labeled alphabetically, starting from the N-terminus. Surface exposed amino acid loops connect the β-strands. The disulfide bridge is formed by two conserved cystein residues that are separated by a stretch of 55-75 amino acids from each other in the primary sequence.

Ig-like domains are protein domains that are similar to the amino acid sequence and structure of Igs. Ig-like domains are categorized into four different topological subtypes that are called "sets": the V-set (antibody variable-domain like), the C1-set (antibody constant-domain 1 like), the C2-set (antibody constant-domain 2 like), and the I-set domain (antibody intermediate-domain like). Structurally, sets differ in the number and size of the β-strands as well as the size and conformation of the loops. A V-set domain is generally larger than C-set domains and possesses a total of 9 β-strands. The β-strands designated as A, B, E, and D are on one sheet and G, F, C, C', and C" on the other β-sheet. The two additional strands that are missing in C1-set domains are located between strand C and D and therefore are called C' and C". Another hallmark of a V-set domain is the A-A' kink in the N-terminal A strand. In many cases a cis-Prolin resides at the kink. Cysteines of V-set folds are generally spaced apart at 65-75 amino acids.

C1- and C2-set folds have a total of seven β-strands and in general, their cysteines are spaced 55-60 amino acids apart in the linear sequence. In case of C1-set domains, the first β-sheet is composed of four β-strands designated as A, B, D, and E, while the second is composed of three β-strands designated as C, F, and G.

C2-set domains combine features of the V- and the C1-set domains: the fold corresponds to the C1-set domain, but amino acid sequences of the β-strands near the C-terminal conserved cystein residue are similar to the V-set domain. Thus, a folding structure arises that forms one β-sheet composed of the β-strands E, B, A and a second β-sheet composed of the strands G, F, C, C'. This architecture generally shows a tighter association between the E and the F strands.

Members of the I-set domain are more closely related to the V-set domains and the fold can be described as a V-set domain which is truncated on one side resulting in a missing C" strand (Natarajan 2015, Bork 1994, Huang 1997).

The transmembrane domain of the CAR may be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules (domains) are on two (or even more) polypeptides then the CAR may have two (or more) transmembrane domains. The splitting key signaling and antigen recognition modules enable for a small molecule-dependent, titratable and reversible control over CAR cell expression (e.g. WO2014127261A1) due to small molecule-dependent heterodimerizing domains in each polypeptide of the CAR.

The cytoplasmic signaling domain (the intracellular signaling domain or the activating endodomain) of the CAR is responsible for activation of at least one of the normal effector functions of the immune cell in which the CAR is expressed, if the respective CAR is an activating CAR (normally, a CAR as described herein refers to an activating CAR). "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR to perform a specialized function. The intracellular signaling domain may include any complete, mutated or truncated part of the intracellular signaling domain of a given protein sufficient to transduce a signal which initiates or blocks immune cell effector functions.

Prominent examples of intracellular signaling domains for use in the CARs include the cytoplasmic signaling sequences of the T cell receptor (TCR) and co-receptors that initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences, primary cytoplasmic signaling domain) and secondly those that act in an antigen-independent manner to provide a secondary or co-stimulatory signal (secondary cytoplasmic signaling sequences, co-stimulatory signaling domain). Therefore, an intracellular signaling domain of a CAR may comprise one or more primary cytoplasmic signaling domains and/or one or more secondary cytoplasmic signaling domains.

Primary cytoplasmic signaling domains that act in a stimulatory manner may contain ITAMs (immunoreceptor tyrosine-based activation motifs).

Examples of ITAM containing primary cytoplasmic signaling domains often used in CARs are that those derived from TCRζ (CD3ζ), FcRgamma, FcRbeta, CD3gamma, CD3delta, CD3epsilon, CD5, CD22, CD79a, CD79b, and CD66d. Most prominent is sequence derived from CD3ζ.

The cytoplasmic domain of the CAR may be designed to comprise the CD3 ζ signaling domain by itself or combined with any other desired cytoplasmic domain(s). The cytoplasmic domain of the CAR can comprise a CD3ζ chain portion and a co-stimulatory signaling region (domain). The co-stimulatory signaling region refers to a part of the CAR comprising the intracellular domain of a co-stimulatory molecule. A co-stimulatory molecule is a cell surface molecule other than an antigen receptor or their ligands that is required for an efficient response of lymphocytes to an antigen. Examples for a co-stimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other with or without a linker in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3ζ and the signaling domain of CD28. In another example the cytoplasmic domain may comprise the signaling domain of CD3ζ and the signaling domain of CD137. In a further example, the cytoplasmic domain may comprise the signaling domain of CD3ζ, the signaling domain of CD28, and the signaling domain of CD137.

As aforementioned either the extracellular part or the transmembrane domain or the cytoplasmic domain of a CAR may also comprise a heterodimerizing domain for the aim of splitting key signaling and antigen recognition modules of the CAR.

The CAR may be further modified to include on the level of the nucleic acid encoding the CAR one or more operative elements to eliminate CAR expressing immune cells by virtue of a suicide switch. The suicide switch can include, for example, an apoptosis inducing signaling cascade or a drug that induces cell death. In one embodiment, the nucleic acid expressing and encoding the CAR can be further modified to express an enzyme such thymidine kinase (TK) or cytosine deaminase (CD). The CAR may also be part of a gene expression system that allows controlled expression of the CAR in the immune cell. Such a gene expression system may be an inducible gene expression system and wherein when an induction agent is administered to a cell being transduced with said inducible gene expression system, the gene expression system is induced and said CAR is expressed on the surface of said transduced cell.

In some embodiments, the endodomain may contain a primary cytoplasmic signaling domains or a co-stimulatory region, but not both. In these embodiments, an immune effector cell containing the disclosed CAR is only activated if another CAR containing the missing domain also binds its respective antigen.

In some embodiment of the invention the CAR may be a "SUPRA" (split, universal, and programmable) CAR, where a "zipCAR" domain may link an intra-cellular costimulatory domain and an extracellular leucine zipper (WO2017/091546). This zipper may be targeted with a complementary zipper fused e.g. to an scFv region to render the SUPRA CAR T cell tumor specific. This approach would be particularly useful for generating universal CAR T cells for various tumors; adapter molecules could be designed for tumor specificity and would provide options for altering specificity post-adoptive transfer, key for situations of selection pressure and antigen escape.

If the CAR is an inhibitory CAR (referred to herein normally as "iCAR"), then said CAR may have the same extracellular and/or transmembrane domains as the activating CAR but differs from the activating CAR with regard to the endodomain.

The at least one endodomain of the inhibitory CAR may be a cytoplasmic signaling domain comprising at least one signal transduction element that inhibits an immune cell or comprising at least one element that induces apoptosis.

Inhibitory endodomains of an iCAR are well-known in the art and have been described e.g. in WO2015075469A1, WO2015075470A1, WO2015142314A1, WO2016055551A1, WO2016097231A1, WO2016193696A1, WO2017058753A1, WO2017068361A1, WO2018061012A1, and WO2019162695A1.

Said at least one signal transduction element that inhibits or may be capable of inhibiting an (effector) immune cell of said iCAR may be a signal transduction element of an immune checkpoint protein.

Said inhibitory signal transduction element may be selected from the groups consisting of:

the immunoglobulin superfamily (IgSF) and tumour necrosis factor receptor superfamily (TNFRSF) including immune checkpoint proteins CD22, CD31, CD33, CD47, CD85A (LIR3), CD85C (LIRE), CD85D (LIR2), CD87J (LIR1), CD85K (LIR5), CD89 (B71), CD94 (KLRD1), CD152 (CTLA4), CD158A (KIR2DL1), CD158B1 (KIR2DL2), CD158B2 (KIR2DL3), CD158D (KIR2DL4), CD158E1 (KIR3DL1), CD158F (KIR2DL5A) CD158K (KIR3DL2), CD158Z (KIR3DL3), CD159a, CD159c, CD160, CD223 (LAG3), CD244 (SLAMF4), CD272 (BTLA), CD274 (PDL1), CD279 (PD1), CD328 (Siglec7), CD329 (Siglec9), CD352 (SLAMF6), CEACAM1, CEACAM2, FcgammaR, G6b-B, KIR2DL5B, KLRG1, LAIR1, PD1H (Vista), PIR-B, Siglec2, Siglec3, Siglec5, Siglec6, Siglec8, Siglec10, Siglec11, Siglec12, TIGIT, TIM2, TIM3, and TLT-1 protein tyrosine phosphatases ACP1, CDC14A, CDC14B, CDC14C, CDC25A, CDC25B, CDC25C, CDKN3, DNAJC6, DUPD1, DUSP1, DUSP10, DUSP11, DUSP12, DUSP13, DUSP14, DUSP15, DUSP16, DUSP18, DUSP19, DUSP2, DUSP21, DUSP22, DUSP23, DUSP26, DUSP27, DUSP28, DUSP3, DUSP4, DUSP5, DUSP6, DUSP7, DUSP8, DUSP9, EPM2A, FIG. 4, GAK, INPP5A, INPP5B, INPP5D, INPP5E, INPP5F, INPP5J, INPP5K, INPPL1, MTM1, MTMR1, MTMR10, MTMR11, MTMR12, MTMR14, MTMR2, MTMR3, MTMR4, MTMR6, MTMR7, MTMR8, MTMR9, OCRL, PALD1, PIP4P1, PIP4P2, PTEN, PTP4A1, PTP4A2, PTP4A3, PTPDC1, PTPMT1, PTPN1, PTPN11, PTPN12, PTPN13, PTPN14, PTPN18, PTPN2, PTPN20, PTPN21, PTPN22, PTPN23, PTPN3, PTPN4, PTPN5, PTPN6, PTPN7, PTPN9, PTPRA, PTPRB, PTPRC, PTPRD, PTPRE, PTPRF, PTPRG, PTPRH, PTPRJ, PTPRK, PTPRM, PTPRN, PTPRN2, PTPRO, PTPRQ, PTPRR, PTPRS, PTPRT, PTPRU, PTPRZ1, RNGTT, SACM1L, SBF1, SBF2, SSH1, SSH2, SSH3, STYX, STYXLL SYNE, SYNJ2, TNS1, TNS2, TNS3, TNS4, TPTE, and TPTE2.

Said at least one signal transduction element that inhibits an immune cell of said iCAR may be also selected from STimulator of INterteron Genes (STING); immunoreceptor tyrosine-based inhibitory motif (ITIM) containing proteins, immunoreceptor tyrosine-based switch motif (ITSM) containing proteins, T cell immunoglobulin and HTM domain (TIGIT), and adenosine receptor (e.g. A2aR).

Said at least one signal transduction element that inhibits an immune cell of said iCAR may be also a tyrosine phosphatase domain from a Src homolog (SH2) domain-containing protein tyrosine phosphatase which is recruited by a phosphorylated Immunoreceptor Tyrosine-based Activation motif (ITIM).

Said at least one signal transduction element that inhibits an immune cell of said iCAR may be also (i) a truncated protein which comprises an SH2 domain from a protein which binds a phosphorylated immunoreceptor tyrosine-based activation motif (ITAM), but lacks a kinase domain; or (ii) a truncated protein which comprises an SH2 domain from a protein which binds a phosphorylated immunoreceptor tyrosine-based inhibition motif (ITIM) but lacks a phosphatase domain; or (iii) a fusion protein which comprises (a) an SH2 domain from a protein which binds a phosphorylated immunoreceptor tyrosine-based activation motif (ITAM) or from a protein which binds a phosphorylated immunoreceptor tyrosine-based inhibition motif (ITIM); and (ii) a heterologous domain. Said heterologous domain may be a phosphatase domain or a kinase domain.

Said at least one element that induces apoptosis may be e.g. a Tumor-necrosis-factor related apoptosis inducing ligand (TRAIL) receptor or a CD200 receptor as described e.g. in detail in WO20160972331A1.

The CARs of the present invention may be designed to comprise any portion or part of the above-mentioned domains as described herein in addition to the spacer as disclosed herein in any order and/or combination resulting in a functional CAR, i.e. a CAR that mediated an immune effector response of the immune effector cell that expresses the CAR as disclosed herein or that as an inhibitory function (iCAR) as disclosed herein.

The term "tagged polypeptide" as used herein refers to a polypeptide that has bound thereto directly or indirectly at least one additional component, i.e. the tag. The tagged polypeptide as used herein is able to bind an antigen expressed on a target cell. The polypeptide may be an antibody or antigen binding fragment thereof that binds to an antigen expressed on the surface of a target cell such as a tumor associated antigen on a cancer cell. The polypeptide of the tagged polypeptide alternatively may a cytokine or a growth factor or another soluble polypeptide that is capable of binding to an antigen of a target cell.

The term "adapter" or "adapter molecule" as used herein refers to a tagged polypeptide that can bind to an antigen of a target cell, e.g. antibody or antigen binding fragment thereof, and has bound thereto directly or indirectly at least one additional component, i.e. the tag. The adapter or adapter molecule may by a tagged antibody or antigen binding fragment thereof, a cytokine or a growth factor or another soluble polypeptide that is capable of binding to an antigen of a target cell.

The tag may be e.g. a hapten or dextran and the hapten or dextran may be bound by the antigen binding domain of the polypeptide comprising an antigen binding domain specific for the tag.

Haptens such as e.g. FITC, biotin, PE, streptavidin or dextran are small molecules that elicit an immune response only when attached to a large carrier such as a protein; the carrier may be one that also does not elicit an immune response by itself. Once the body has generated antibodies to a hapten-carrier adduct, the small-molecule hapten may also be able to bind to the antibody, but it will usually not initiate an immune response; usually only the hapten-carrier adduct can do this.

But the tag may also be a peptide sequence e.g. chemically or recombinantly coupled to the polypeptide part of the tagged polypeptide. The peptide may be selected from the group consisting of c-Myc-tag, Strep-Tag, Flag-Tag, and Polyhistidine-tag. The tag may also be streptavidin. The tag portion of the tagged polypeptide is only constrained by being a molecular that can be recognized and specifically bound by the antigen binding domain specific for the tag of the CAR. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv.

The term "antibody" as used herein is used in the broadest sense to cover the various forms of antibody structures including but not being limited to monoclonal and polyclonal antibodies (including full length antibodies), multi-specific antibodies (e.g. bispecific antibodies), antibody fragments, i.e. antigen binding fragments of an antibody, immunoadhesins and antibody-immunoadhesin chimeras, that specifically recognize (i.e. bind) an antigen. "Antigen binding fragments" comprise a portion of a full-length antibody, preferably the variable domain thereof, or at least the antigen binding site thereof ("an antigen binding fragment of an antibody"). Examples of antigen binding fragments include Fab (fragment antigen binding), scFv (single chain fragment variable), single domain antibodies, diabodies, dsFv, Fab', diabodies, single-chain antibody molecules, and multispecific antibodies formed from antibody fragments. The terms "having specificity for", "specifically binds" or "specific for" with respect to an antigen-binding domain of an antibody, of a fragment thereof or of a CAR refer to an antigen-binding domain which recognizes and binds to a specific antigen, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain that specifically binds to an antigen may bind also to different allelic forms of the antigen (allelic variants, splice variants, isoforms etc.). This cross reactivity is not contrary to the definition of that antigen-binding domain as specific. T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are several subsets of T cells, each with a distinct function.

T helper cells (TH cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate a different type of immune response. Signaling from the APC directs T cells into particular subtypes.

Cytotoxic T cells (TC cells, or CTLs) destroy virally infected cells and tumor cells, and are also implicated in transplant rejection. These cells are also known as CD8+ T cells since they express the CD8 glycoprotein at their surface. These cells recognize their targets by binding to antigen associated with MHC class I molecules, which are present on the surface of all nucleated cells.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—Foxp3+ Treg cells and Foxp3-Treg cells.

Natural killer T cells (NKT cells—not to be confused with natural killer cells of the innate immune system) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both Th and Tc cells (i.e., cytokine production and release of cytolytic/cell killing molecules).

The term "natural killer cells (NK cells)" are defined as large granular lymphocytes (LGL) and constitute the third kind of cells differentiated from the common lymphoid progenitor-generating B and T lymphocytes. NK cells are known to differentiate and mature in the bone marrow, lymph nodes, spleen, tonsils, and thymus, where they then enter into the circulation. NK cells differ from natural killer T cells (NKTs) phenotypically, by origin and by respective effector functions; often, NKT cell activity promotes NK cell activity by secreting IFNγ. In contrast to NKT cells, NK cells do not express T-cell antigen receptors (TCR) or pan T marker CD3 or surface immunoglobulins (Ig) B cell receptors, but they usually express the surface markers CD16 (FcγRIII) and CD56 in humans, NK1.1 or NK1.2 in C57BL/6 mice. Up to 80% of human NK cells also express CD8. Continuously growing NK cell lines can be established from cancer patients and common NK cell lines are for instance NK-92, NKL and YTS. The terms "immune cell" or "immune effector cell" may be used interchangeably and refer to a cell that may be part of the immune system and executes a particular effector function such as alpha-beta T cells, NK cells, NKT cells, B cells, innate lymphoid cells (ILC), cytokine induced killer (CIK) cells, lymphokine activated killer (LAK) cells, gamma-delta T cells, monocytes or macrophages. Preferentially these immune cells are human immune cells. Preferred immune cells are cells with cytotoxic effector function such as alpha-beta T cells, NK cells, NKT cells, ILC, CIK cells, LAK cells or gamma-delta T cells. Most preferred immune effector cells are T cells and NK cells. "Effector function" means a specialized function of a cell, e.g. in a T cell an effector function may be cytolytic activity or helper activity including the secretion of cytokines.

As used herein, the term "antigen" is intended to include substances that bind to or evoke the production of one or more antibodies and may comprise, but is not limited to, proteins, peptides, polypeptides, oligopeptides, lipids, carbohydrates such as dextran, haptens and combinations thereof, for example a glycosylated protein or a glycolipid. The term "antigen" as used herein refers to a molecular entity that may be expressed on the surface of a target cell and that can be recognized by means of the adaptive immune system including but not restricted to antibodies or TCRs, or engineered molecules including but not restricted to endogenous or transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The term "epitope" means the part of an antigen, e.g. a soluble antigen, that may be recognized and specifically bound by antibodies or antigen bindings fragments thereof (antigen binding domains).

The tumor associated antigen (TAA) as used herein refers to an antigenic substance produced in tumor cells. Tumor associated antigens are useful tumor or cancer markers in identifying tumor/cancer cells with diagnostic tests and are potential candidates for use in cancer therapy. Preferentially, the TAA may be expressed on the cell surface of the tumor/cancer cell, so that it may be recognized by the antigen binding receptor as disclosed herein.

The term "target cell" as used herein refers to cell which expresses an antigen on its cell surface that should be recognized (bound) by the antigen binding domain of the CAR as disclosed herein or by the antigen binding domain of the tag of the tagged polypeptide as disclosed herein. Said target cell may be e.g. a cancerous cell or a cell associated with an autoimmune disease or a cell associated with an infectious disease.

Immunotherapy is a medical term defined as the "treatment of disease by inducing, enhancing, or suppressing an immune response". Immunotherapies designed to elicit or amplify an immune response are classified as activation immunotherapies, while immunotherapies that reduce or suppress are classified as suppression immunotherapies. Cancer immunotherapy as an activating immunotherapy attempts to stimulate the immune system to reject and destroy tumors. Adoptive cell transfer uses cell-based, preferentially T cell-based or NK cell-based cytotoxic responses to attack cancer cells. T cells that have a natural or genetically engineered reactivity to a patient's cancer are generated in-vitro and then transferred back into the cancer patient. Then the immunotherapy is referred to as "CAR immunotherapy" or in case of use of T cells only as "CAR T cell therapy" or "CAR T cell immunotherapy".

The term "treatment" as used herein means to reduce the frequency or severity of at least one sign or symptom of a disease.

The terms "therapeutically effective amount" or "therapeutically effective population" mean an amount of a cell population which provides a therapeutic benefit in a subject.

As used herein, the term "subject" refers to an animal. Preferentially, the subject is a mammal such as mouse, rat, cow, pig, goat, chicken dog, monkey or human. More preferentially, the individual is a human. The subject may be a subject suffering from a disease such as cancer. The term "expression" as used herein is defined as the transcription and/or translation of a particular nucleotide sequence driven by its promoter in a cell.

The terms "engineered cell" and "genetically modified cell" as used herein can be used interchangeably. The terms mean containing and/or expressing a foreign gene or nucleic acid sequence which in turn modifies the genotype or phenotype of the cell or its progeny. Especially, the terms refer to the fact that cells, preferentially T cells can be manipulated by recombinant methods well known in the art to express stably or transiently peptides or proteins which are not expressed in these cells in the natural state. For example, T cells, preferentially human T cells are engineered to express an artificial construct such as a chimeric antigen receptor on their cell surface.

The term "cancer" is known medically as a malignant neoplasm. Cancer is a broad group of diseases involving unregulated cell growth and includes all kinds of leukemia. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans.

EXAMPLES

The following examples are intended for a more detailed explanation of the invention but without restricting the invention to these examples.

Example 1: Construction and Expression of C2-Set Ig-Like Domain Spacer CARS in HEK293 and Primary Human T Cells Commercial gene synthesis in combination with an optimization algorithm for codon usage in humans (ATUM) was used to construct C2-set Ig-like domain spacer and control CAR genes targeting the CD20 antigen. The CD20-specific CARs comprised as a binding domain SEQ ID NO:5, which binds a well-characterized membrane-proximal epitope. All antigen binding domains contained a (G4S)3-linker between the VL and the VH regions. To facilitate receptor trafficking to the plasma membrane, a human CD8α or CD8β leader signaling peptide was added N-terminally to the respective scFv sequence. The spacer region downstream of the scFv for the state-of-the-art control CD20 CAR encompassed the CD8a hinge (45 amino acids). Spacers bearing C2-set Ig-like domains were derived from the Siglec family and designed based on the protein sequences extracted from UniProt and the plasma membrane-proximal domains were incorporated into the CAR architecture. Thus, the Siglec-3 spacer comprised the amino acids 145-259 of the parent protein with a C169S mutation to abrogate unspecific disulfide-bond formation (SEQ ID NO:12). The Siglec-4 spacer contained the amino acids 238-519 (SEQ ID NO:1), the Siglec-7.1 spacer the amino acids 150-353 (SEQ ID NO:2), the Siglec-7.2 spacer the amino acids 234-353 (SEQ ID NO:3), and the Siglec-8 spacer the amino acids 241-363 (SEQ ID NO:4) of the respective parent protein. All spacers were linked to the transmembrane domain of human CD8α, the intracellular domain of 4-1BB, and the CD3 signaling domain as derived from UniProt (SEQ ID NO:6-9; SEQ ID NO:13). The CAR genes were fused to a Furin-P2A sequence to include co-expression of the truncated low affinity nerve growth factor receptor (ΔLNGFR). Transgene expression was promoted by the PGK promoter located upstream of the CAR gene.

To confirm correct translation and surface expression of the constructs, bicistronic lentiviral expression vectors were generated (FIGS. 1A and 1B). After transfection of the DNA constructs into HEK293T cells, detection of the reporter protein ΔLNGFR confirmed successful transcription and translation of the CAR cassette, while direct staining of the CAR with a CD20 CAR detection reagent (PE) visualized surface expression of the CAR constructs. All constructs showed both ΔLNGFR and CAR expression in >80% of HEK293T cells (FIG. 2A). To analyse CAR construct expression in primary T cells, peripheral blood mononuclear cells (PBMCs) were isolated from buffy coats by density gradient centrifugation. T cells were purified from PBMCs applying the Pan T Cell Isolation Kit, human (Miltenyi Biotec) and activated in TexMACS™ Medium (Miltenyi Biotec) supplemented with T Cell TransAct™, human (Miltenyi Biotec) and 100 IU/ml of recombinant Human IL-2 IS, research grade (Miltenyi Biotec). T cells were transduced 24 h after activation using VSV-G pseudotyped lentiviral particles. 3 days post activation, T Cell TransAct™, human and excess viral vector were removed and T cells were cultured in TexMACS™ Medium only supplemented with IL-2. T cells were expanded for 12 days and used directly for in vitro assays. The ΔLNGFR reporter protein was expressed in all cases demonstrating effective lentiviral transduction of the T cells and translation of the expression cassette (FIG. 2B). While three CAR constructs showed CAR expression levels comparable to the CD8a spacer CAR control (CD20_hl_Sig4 CAR, CD20_hl_Sig7.2 CAR, CD20_hl_Sig8 CAR), no CD20_hl_Sig7.1 CAR expression was detectable and the CD20_hl_Sig3 CAR was expressed on only 5% of the T cells.

Example 2: C2-Set Ig-Like Domain Spacer CARs Targeting CD20 are Functional in Primary Human T Cells $2 \times 10^5$ T cells, each expressing different Siglec-based spacer CAR constructs or a CD8a hinge spacer CAR control, were incubated with $2 \times 10^5$ CD20+ Raji cells in 200 µl TexMACS™ Medium at 37° C. In addition, the medium was supplemented with 20 µl of a CD107a specific antibody. After 1 h of incubation the protein transport inhibitors Monensin and Brefeldin A (BD Biosciences) were added as recommended for 4 h. After this incubation period, cells were washed and first surface stained with LNGFR specific antibodies to label transduced T cells and subsequently intracellularly stained for TNF-α using the Inside Stain Kit and a TNF-α specific antibody (all Miltenyi Biotec). Cells were then measured by flow cytometry. For analysis of the T cell activation/exhaustion markers TIM3, LAG3 and PD1, $1 \times 10^5$ CART cells were inoculated with $2 \times 10^5$ CD20+ Raji cells in 200 µl TexMACS™ Medium at 37° C. for 24 h. Subsequently T cells were stained and analysed by flow cytometry. Only CAR T cells co-cultured with CD20+ target cells showed significant degranulation (FIG. 2C). Strongest degranulation could be observed for the CD8a and Siglec-4 spacer variants with around 35% of CD107α positive cells. The Siglec-7.2 spacer CAR produced an intermediate amount of CD107α at 20% positive cells and the Siglec-8 variant showed a lower 10% degranulation that was still significantly different to the negative control cells. Similar to the degranulation analysis, the proportion of ALNGFR+/TNF-α+ cells was also highest in CD8a spacer CAR T cells (32%, FIG. 2 D) but markedly fewer CD20_hl_Sig4 CART cells expressed TNF-α (18% positive cells), followed by Siglec-7.2 and Siglec-8 spacer CARS. Again, no unspecific activation could be observed in the controls. We also assessed the activation state of the modified T cells by analysing TIM3, LAG3 and PD1 surface expression. CD20+ Raji cells were co-cultured with CAR T cells for 24 h at an E:T ratio of 1:2. The CD8a and Siglec-4 spacer CAR modified T cells contained the largest fraction of TIM3/LAG3/PD1 triple positive cells (FIG. 2E).

Example 3: C2-Set Ig-Like Domain Spacer CARs Targeting TSPAN8 are Functional in Primary Human T Cells The Siglec-based spacers were tested in the context of a solid tumour model to target novel pancreatic ductal adenocarcinoma (PDAC) target antigens CD66c and TSPAN8. TSPAN8 has two extracellular loops extending from the membrane that span 24 and 96 amino acids respectively, the larger having two interconnecting disulfide bonds. Thus, the whole protein is very membrane proximal. On the other hand, CD66c is a glycophosphatidylinositol anchored protein and consists of two C2-set domains and one V-set domain. In consequence it extends further into the extracellular space compared to TSPAN8. In addition, the epitope of the aCD66c scFv is localized on the outer N terminal V-set domain. In summary, TSPAN8 can be considered a membrane proximal target, while CD66c is a membrane distal target.

Figures 3A, 3B:
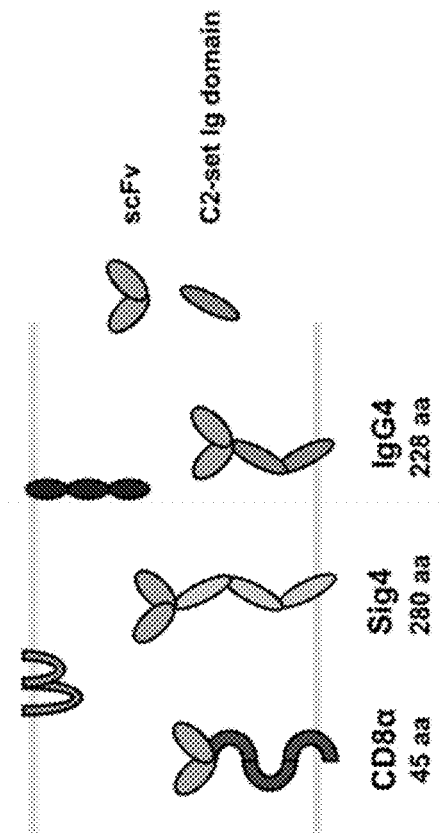
FIGS. 3A and 3B depict the design of C2-set Ig-like domain containing CARs specific for CD66c and TSPAN8.

Siglec-4 spacer CARs targeting TSPAN8 (SEQ ID NO:11) or CD66c were generated by replacing the scFv from the CD20_hl_Sig4 CAR (SEQ ID NO:6) through the scFv derived from the TSPAN8-reactive monoclonal antibody REA443 (SEQ ID NO:10) or the CD66c-reactive monoclonal antibody REA414 (Miltenyi Biotec). Additionally, we incorporated in our experiments CD66c and TSPAN8 specific CD8a spacer CARs and a TSPAN8 specific IgG4 CH2-CH3 spacer CAR of 228 amino acids (FIGS. 3A and 3B). In the case of the IgG4 CH2 domain, the APEFLG sequence was replaced by APPVA from IgG2 and an N279Q mutation was introduced to remove glycosylation at this site (Hudecek et al., 2015).

GFP+/Luc+ AsPC1 target cells were inoculated in 96-well plates at $2.5 \times 10^4$ cells per well in TexMACS™ Medium. CAR T cells or untransduced Mock T cells were added with at an E:T ratio of 2:1. The amount of T cells in the Mock control was adjusted to the number of total T cells in the CAR group with the highest total cell count. Cytotoxicity was measurement as the decrease of green surface area as assessed by the IncuCyte® S3 Live-Cell Analysis System (Sartorius). Measured values were normalized to the start of the experiment. After 24 h a supernatant sample was taken for cytokine measurements using the MACSPlex Cytokine 12 Kit. At the end of the experiment expression of LAG3, PD1 and 4-1BB were measured using a MACSQuant Analyzer 8 (Miltenyi Biotec). Specific endpoint killing was calculated from the green surface area values with the following formula:

$$\text{specific killing}[\%] = 100 - \left(100 * \frac{\text{green area Mock}}{\text{green area CAR}}\right)$$

Figures 5A, 5B, 5C:
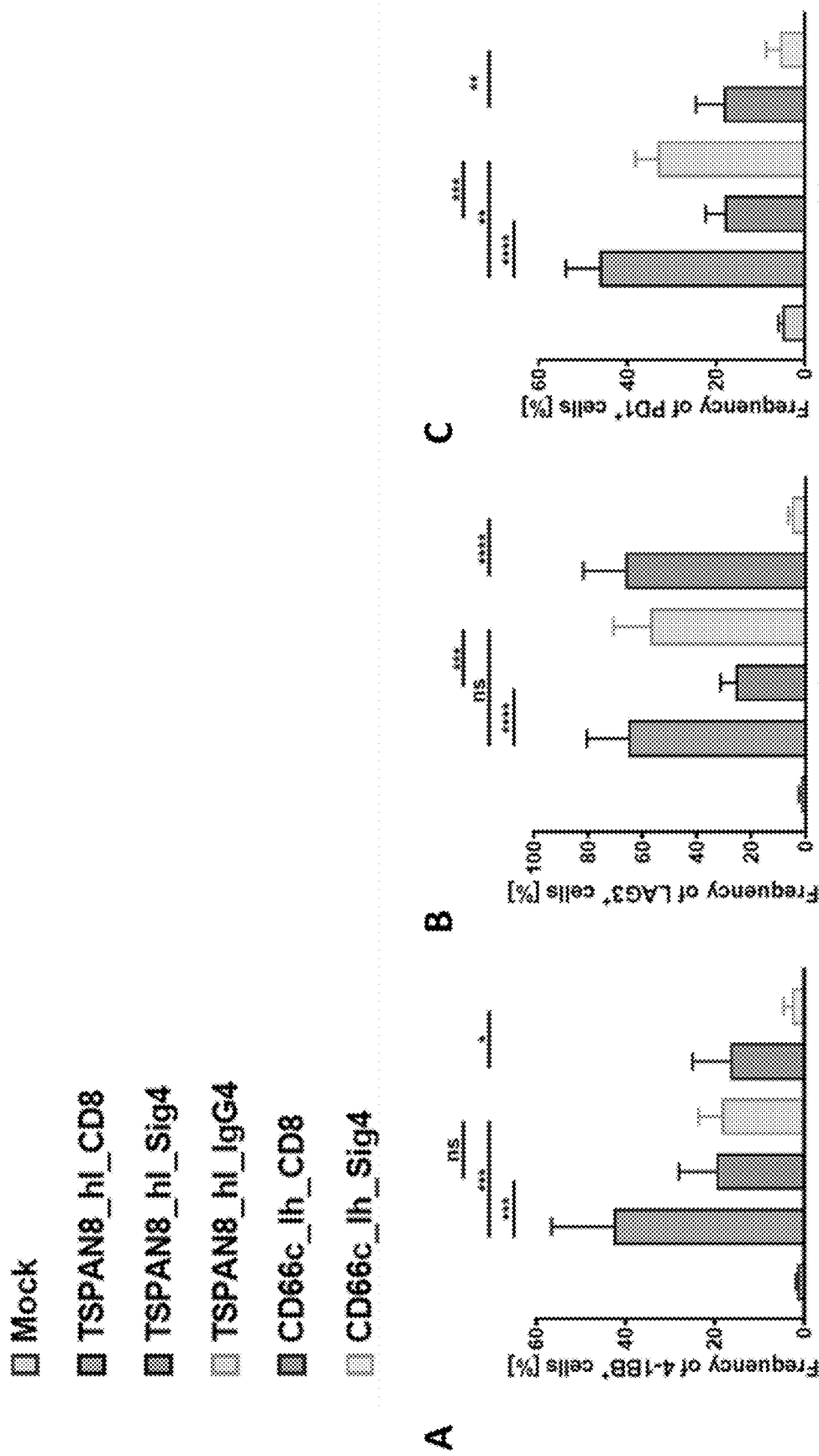
FIGS. 5A-C depict in vitro comparison of T cells transduced with TSPAN8 and CD66c CAR constructs, incorporating different spacer domains. Frequency of (FIG. 5A) 4-1BB, (FIG. 5B) LAG3 and (FIG. 5C) PD1 positive CAR T cells was analyzed at the end of the cytolytic evaluation with AsPC1 cells by flow cytometry. Shown is the mean±SD. ns>0.05, *p<0.05, p<0.01, *p<0.001 and ****p<0.0001 [one-way ANOVA, multiple comparisons].

Both, the CD66c_lh_Siglec-4 CAR T cells, as well as the untransduced control T cells showed no specific killing of target cells, while the CD66c_lh_CD8 CAR showed a specific endpoint killing of 42%, (FIG. 4B). On the other hand, when targeting the membrane proximal TSPAN8, the Siglec-4 spacer CART cells showed a similar killing to that of the TSPAN8_hl_CD8a CAR T cells approaching 60% endpoint killing. In contrast, CAR T cells modified with a TSPAN8 CAR with the alternative long IgG4 CH2-CH3 spacer exhibited only 40% killing at the end of the experiment, showing the weakest cytotoxicity of all tested TSPAN8 CAR T cells. The CD66c_lh_Sig4 CAR T cells, which showed no cytotoxicity, also expressed no activation markers (FIGS. 5A-C). The strongest upregulation of activation markers 4-1BB, LAG3 and PD-1 was observed in TSPAN8_hl_CD8a CAR T cells. Interestingly and unexpectedly, the TSPAN8 specific Siglec-4 CAR T cells displayed a lower expression of activation markers, even though the cytotoxicity equalled that of the CD8a spacer CAR T cells. This difference between the CD8a and the Siglec-4 spacer CAR T cells was even more striking at the cytokine level (FIGS. 6A and 6B). The TSPAN8_hl_CD8 CAR T cells released markedly higher levels of cytokines than the other CAR T cells. The TSPAN8_hl_Sig4 CART cells, despite displaying similar killing kinetics to the TSPAN8 CD8a CAR T cells, secreted over 10-fold lower levels of cytokines after antigen-specific stimulation, which was very surprising, given the same observed cytotoxicity as the TSPAN8 CD8a CAR T cells.

Figure 7:
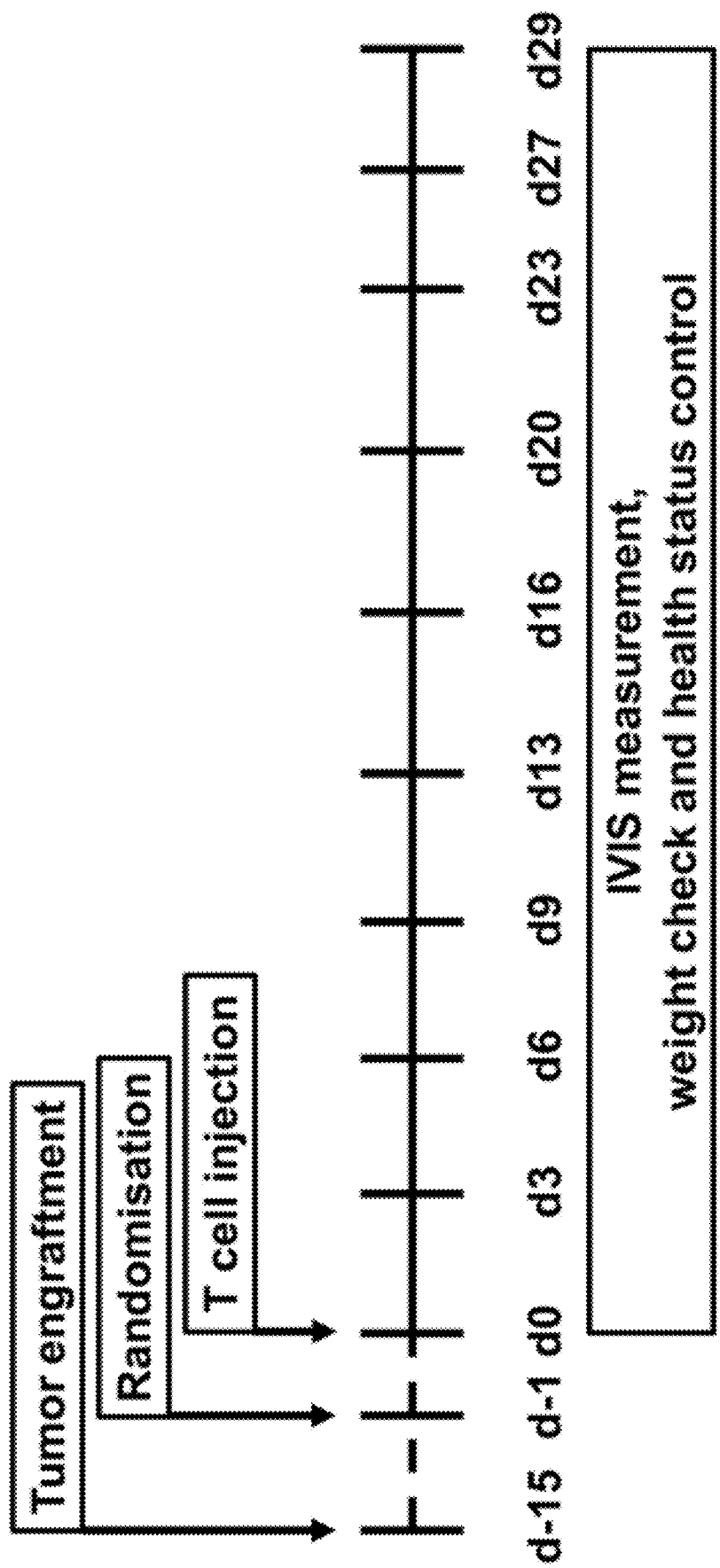
FIG. 7 outlines the experimental design to study the therapeutic potential of different spacer CAR T cells in a subcutaneous xenograft model.

Example 4: C2-Set Ig-Like Domain Spacer CARs Targeting TSPAN8 are Highly Functional in an In Vivo Solid Tumor Model We investigated the functionality of three TSPAN8 specific CAR constructs TSPAN8_hl_Sig4 CAR, TSPAN8_hl_IgG4 CAR and TSPAN8 CD8a CAR) in vivo in a pre-clinical PDAC tumor model. For AsPC1 GFP+/Luc+ cell line derived tumors $1 \times 10^6$ cells were injected subcutaneously in the right flank of NOD SCID gamma (NSG; NOD.Cg-PrkdcscidIl2rgtm1Wjl/SzJ) mice (Jackson Laboratory, provided by Charles River). When tumors reached a size of 25 mm$^2$, $5 \times 10^6$ CART cells were injected into the tail vein. The amount of injected untransduced Mock T cells was adjusted to the number of total T cells in the CAR group with the highest total cell count (FIG. 7).

Figure 8A:
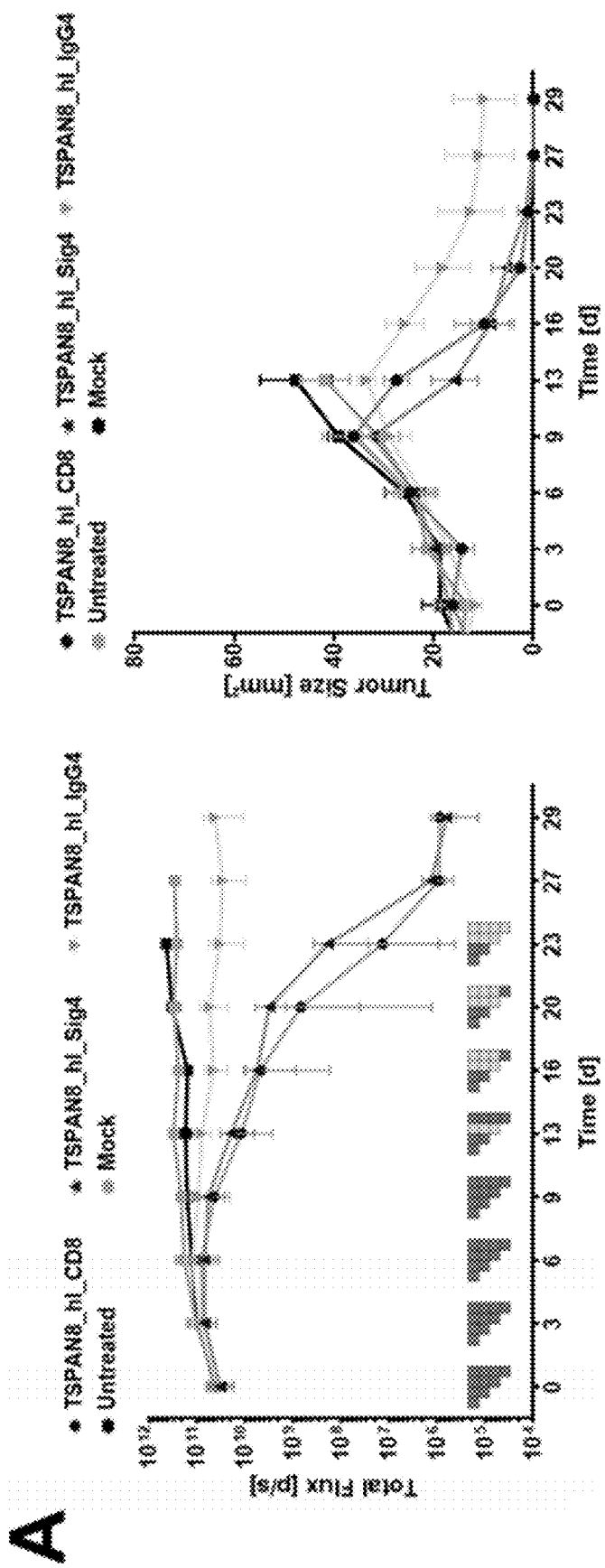
FIGS. 8A and 8B show that the TSPAN8 specific Siglec-4 spacer CAR T cells exhibit the same anti-tumor efficacy as the CD8a spacer CAR T cells, while retaining a more memory-like phenotype.
Figure 8B:
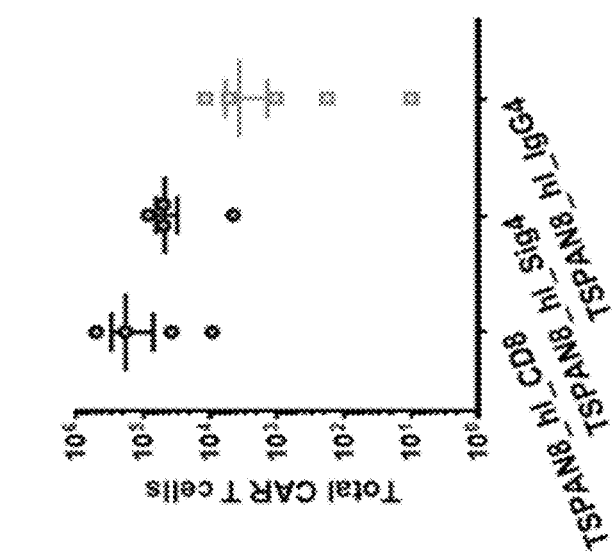
Figure 8B:
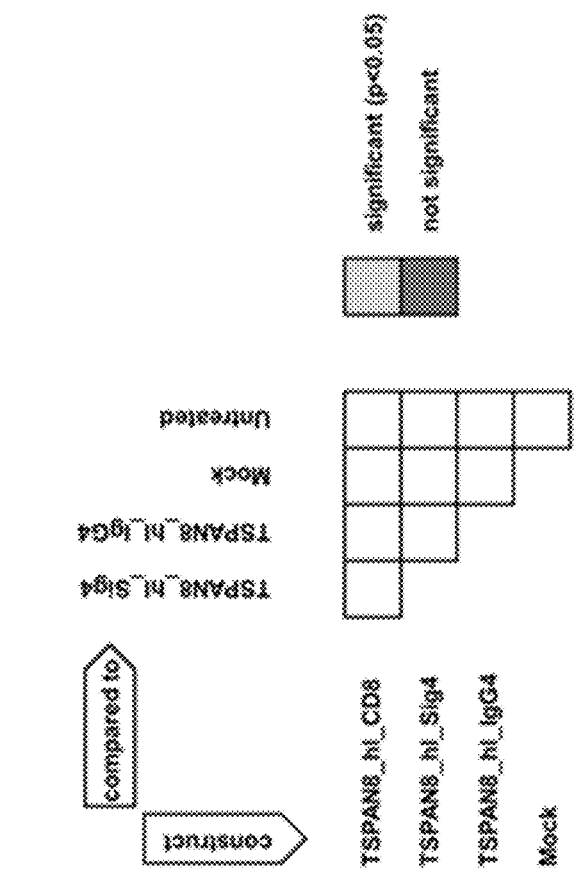

Therapeutic response was measured longitudinally using the IVIS Lumina in vivo imaging system (PerkinElmer) after intraperitoneal injection of 100 µL (30 mg/mL) D-Luciferin (Potassium Salt, LUCK-2G, GoldBio) and additionally by manual caliper measurement (FIGS. 8A and 8B). All measures to secure the well-being of mice were executed following the relevant animal use guidelines and ethical regulations. Upon reaching the endpoint (weight loss of >19%, paralysis, stress score of >20 or end-point of the experiment, Day 20 for the lymphoma model and Day 29 for the pancreatic model), animals were euthanized according to guidelines and post-mortem analysis was performed in order to determine tumor burden, persistence and killing of the different CAR T cell constructs. Therefore, spleen was dissociated using the gentleMACS™ Octo Dissociator with Heaters according to the manufacturers protocol (Miltenyi Biotec). The cell suspensions were filtered through a 70 µm pore size MACS SmartStrainer (Miltenyi Biotec) and following red blood cell lysis on spleen single cell suspensions using Red Blood Cell Lysis Solution (Miltenyi Biotec), samples were stained and analysis was conducted on a MACSQuant Analyzer 8.

Figure 9:
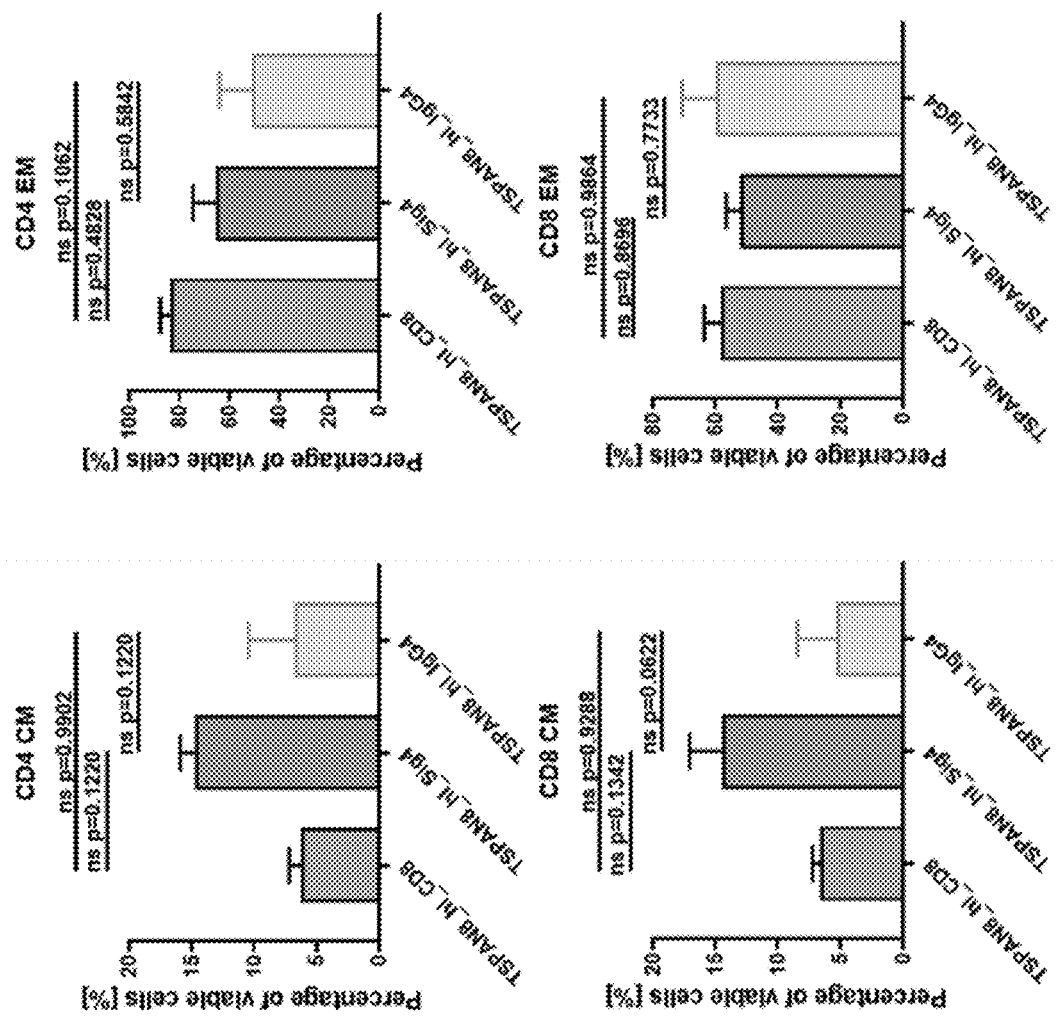
FIG. 9 depicts phenotypic characterization of TSPAN8-specific CAR T cells incorporating different spacers following in vivo therapeutic treatment. Upon reaching humane endpoint criteria, the spleen of each animal and in each mouse cohort was processed into a single cell suspension and the phenotype of the infiltrating human immune cells was determined. Compared to the CD8 spacer and IgG4 spacer CAR T cell cohort, Siglec-4 spacer CAR-transduced T cells displayed a higher level of central memory cells. n=4 Shown is the mean±SD. ns>0.05, *p<0.05, p<0.01, *p<0.001 and ****p<0.0001 [one-way ANOVA, multiple comparisons].

Untransduced (Mock) T cells did not display a therapeutic benefit over the untreated group (FIGS. 8A-B). All mice from these two groups had to be sacrificed before the end of the experiment as tumor ulcerations began to become established. The therapeutic effect for the CD8a and Siglec-4 CARs became apparent in BLI measurements from day 6 onwards. The tumor burden within the groups treated with the CD8a and Siglec-4 spacer CARs decreased in a comparable manner and reached baseline by the end of the experiment 29 days after T cell injection. At the same time, tumor growth was controlled by the IgG4 CH2-CH3 spacer group, but there was no tumor clearance as seen with the other groups. Persistence of CAR T cells could be demonstrated in the spleens of all CAR T cell treated groups with the highest amounts found in the CD8α spacer CAR and Siglec-4 spacer CAR groups (FIG. 9). A markedly lower amount of CAR T cells could be recovered from the IgG4 spacer CAR group. Interestingly, when the phenotype of the human T cells was examined the proportion of TCM (central memory T cells) was twice as high in CD4 and CD8 CART cells of the Siglec-4 spacer CAR group as compared to the CD8α spacer CAR T cells (FIG. 9). This is of particular interest as the TCM phenotype is associated with better overall remission and decreased likelihood of relapse in a clinical context.

REFERENCES

Gross, G., Waks, T., and Eshhar, Z. (1989). Expression of immunoglobulin-T-cell receptor chimeric molecules as functional receptors with antibody-type specificity. *Proceedings of the National Academy of Sciences of the United States of America* 86(24), 10024-10028. doi: 10.1073/pnas.86.24.10024.

Hudecek, M., Sommermeyer, D., Kosasih, P. L., Silva-Benedict, A., Liu, L., Rader, C., et al. (2015). The nonsignaling extracellular spacer domain of chimeric antigen receptors is decisive for in vivo antitumor activity. *Cancer immunology research* 3(2), 125-135. doi: 10.1158/2326-6066. CIR-14-0127.

Patel, S. D., Moskalenko, M., Smith, D., Maske, B., Finer, M. H., and McArthur, J. G. (1999). Impact of chimeric immune receptor extracellular protein domains on T cell function. *Gene therapy* 6(3), 412-419. doi: 10.1038/sj.gt.3300831.

Watanabe, N., Bajgain, P., Sukumaran, S., Ansari, S., Heslop, H. E., Rooney, C. M., et al. (2016). Fine-tuning the CAR spacer improves T-cell potency. *Oncoimmunology* 5(12), e1253656-e1253656. doi: 10.1080/2162402X.2016.1253656.

Krummel M F and Cahalan M D (2010) The Immunological Synapse: a Dynamic Platform for Local Signaling. J Clin Immunol 30:364-72

Garcia K C, Degano M, Stanfield R L, Brunmark A, Jackson M R, Peterson P A, Teyton L, Wilson I A. An αβ T cell receptor structure at 2.5A resolution and its orientation in the TCR-MHC complex. Science. 1996; 274:209-219

Hudecek M, Lupo-Stanghellini M T, Kosasih P L, Sommermeyer D, Jensen M C, Rader C, Riddell S R. (2013) Receptor Affinity and Extracellular Domain Modifications Affect Tumor Recognition by ROR1-specific Chimeric Antigen Receptor T Cells. Clin Cancer Res 19:3153-64.

Natarajan, K.; Mage, M. G.; and Margulies, D. H. (April 2015) Immunoglobulin Superfamily. In: eLS. John Wiley & Sons, Ltd: Chichester.

Bork, P.; Holm, L.; Sander C. (September 1994) The Immunoglobulin Fold. Structural Classification, Sequence Patterns and Common Core Huang, Z.; Li, S.; Korngold, R. (1997) Imunoglobulin Superfamily Proteins: Structure, Mechanisms, and Drug Discovery

What is claimed is:

1. A CAR comprising:
   a) an antigen binding domain specific for an antigen,
   b) a spacer,
   c) a transmembrane domain, and
   d) an intracellular signaling domain,
   wherein said spacer consists of 3 C2-set Ig-like domains, wherein said 3 C2-set Ig-like domains comprise the 3 consecutive plasma membrane-proximal C2-set Ig-like domain of sialic acid binding Ig-like lectin 4 (Siglec-4).

2. The CAR according to claim 1, wherein said antigen is an antigen expressed on the surface of a target cell.

3. The CAR according to claim 1, wherein said antigen binding domain and said spacer are from different proteins.

4. The CAR according to claim 1, wherein said spacer comprises SEQ ID NO: 1.

5. The CAR according to claim 1, wherein said antigen binding domain is a scFv.

6. The CAR according to claim 1, wherein said intracellular signaling domain comprises a primary signaling domain and a co-stimulatory signaling domain.

7. The CAR according to claim 1, wherein said antigen binding domain is specific for CD20.

8. The CAR according to claim 7, wherein said antigen binding domain is a scFv.

9. The CAR according to claim 8, wherein said scFV has the sequence of SEQ ID NO: 5.

10. The CAR according to claim 1, wherein said antigen binding domain is specific for TSPAN8.

11. The CAR according to claim 10, wherein the antigen binding domain has the sequence of SEQ ID NO: 10.

12. The CAR according to claim 1, wherein said target cell is a cancer cell.

* * * * *

SEQUENCE LISTING

```
<160> NUMBER OF SEQ ID NOS: 13

<210> SEQ ID NO 1
<211> LENGTH: 279
<212> TYPE: PRT
<213> ORGANISM: artificial sequence
<220> FEATURE:
<223> OTHER INFORMATION: Siglec-4 (238-516) spacer

<400> SEQUENCE: 1

Tyr Pro Pro Val Ile Val Glu Met Asn Ser Ser Val Glu Ala Ile Glu
1               5                   10                  15

Gly Ser His Val Ser Leu Leu Cys Gly Ala Asp Ser Asn Pro Pro Pro
                20                  25                  30

Leu Leu Thr Trp Met Arg Asp Gly Thr Val Leu Arg Glu Ala Val Ala
            35                  40                  45

Glu Ser Leu Leu Leu Glu Leu Glu Glu Val Thr Pro Ala Glu Asp Gly
        50                  55                  60

Val Tyr Ala Cys Leu Ala Glu Asn Ala Tyr Gly Gln Asp Asn Arg Thr
65                  70                  75                  80

Val Gly Leu Ser Val Met Tyr Ala Pro Trp Lys Pro Thr Val Asn Gly
                85                  90                  95

Thr Met Val Ala Val Glu Gly Glu Thr Val Ser Ile Leu Cys Ser Thr
```

```
            100                 105                 110
Gln Ser Asn Pro Asp Pro Ile Leu Thr Ile Phe Lys Glu Lys Gln Ile
        115                 120                 125

Leu Ser Thr Val Ile Tyr Glu Ser Glu Leu Gln Leu Glu Leu Pro Ala
        130                 135                 140

Val Ser Pro Glu Asp Asp Gly Glu Tyr Trp Cys Val Ala Glu Asn Gln
145                 150                 155                 160

Tyr Gly Gln Arg Ala Thr Ala Phe Asn Leu Ser Val Glu Phe Ala Pro
                165                 170                 175

Val Leu Leu Leu Glu Ser His Cys Ala Ala Ala Arg Asp Thr Val Gln
        180                 185                 190

Cys Leu Cys Val Val Lys Ser Asn Pro Glu Pro Ser Val Ala Phe Glu
        195                 200                 205

Leu Pro Ser Arg Asn Val Thr Val Asn Glu Ser Glu Arg Glu Phe Val
        210                 215                 220

Tyr Ser Glu Arg Ser Gly Leu Val Leu Thr Ser Ile Leu Thr Leu Arg
225                 230                 235                 240

Gly Gln Ala Gln Ala Pro Pro Arg Val Ile Cys Thr Ala Arg Asn Leu
                245                 250                 255

Tyr Gly Ala Lys Ser Leu Glu Leu Pro Phe Gln Gly Ala His Arg Leu
        260                 265                 270

Met Trp Ala Lys Ile Gly Pro
        275
```

<210> SEQ ID NO 2
<211> LENGTH: 204
<212> TYPE: PRT
<213> ORGANISM: artificial sequence
<220> FEATURE:
<223> OTHER INFORMATION: Siglec-7.1 (150-336) spacer

<400> SEQUENCE: 2

```
Pro Asn Ile Leu Ile Pro Gly Thr Leu Glu Ser Gly Cys Phe Gln Asn
1                   5                   10                  15

Leu Thr Cys Ser Val Pro Trp Ala Cys Glu Gln Gly Thr Pro Pro Met
            20                  25                  30

Ile Ser Trp Met Gly Thr Ser Val Ser Pro Leu His Pro Ser Thr Thr
        35                  40                  45

Arg Ser Ser Val Leu Thr Leu Ile Pro Gln Pro Gln His His Gly Thr
    50                  55                  60

Ser Leu Thr Cys Gln Val Thr Leu Pro Gly Ala Gly Val Thr Thr Asn
65                  70                  75                  80

Arg Thr Ile Gln Leu Asn Val Ser Tyr Pro Pro Gln Asn Leu Thr Val
                85                  90                  95

Thr Val Phe Gln Gly Glu Gly Thr Ala Ser Thr Ala Leu Gly Asn Ser
            100                 105                 110

Ser Ser Leu Ser Val Leu Glu Gly Gln Ser Leu Arg Leu Val Cys Ala
        115                 120                 125

Val Asp Ser Asn Pro Pro Ala Arg Leu Ser Trp Thr Trp Arg Ser Leu
    130                 135                 140

Thr Leu Tyr Pro Ser Gln Pro Ser Asn Pro Leu Val Leu Glu Leu Gln
145                 150                 155                 160

Val His Leu Gly Asp Glu Gly Glu Phe Thr Cys Arg Ala Gln Asn Ser
                165                 170                 175

Leu Gly Ser Gln His Val Ser Leu Asn Leu Ser Leu Gln Gln Glu Tyr
```

```
                180                 185                 190
Thr Gly Lys Met Arg Pro Val Ser Gly Val Leu Leu
        195                 200

<210> SEQ ID NO 3
<211> LENGTH: 120
<212> TYPE: PRT
<213> ORGANISM: artificial sequence
<220> FEATURE:
<223> OTHER INFORMATION: Siglec-7.2 (234-336) spacer

<400> SEQUENCE: 3

Leu Asn Val Ser Tyr Pro Pro Gln Asn Leu Thr Val Thr Val Phe Gln
1               5                   10                  15

Gly Glu Gly Thr Ala Ser Thr Ala Leu Gly Asn Ser Ser Ser Leu Ser
            20                  25                  30

Val Leu Glu Gly Gln Ser Leu Arg Leu Val Cys Ala Val Asp Ser Asn
        35                  40                  45

Pro Pro Ala Arg Leu Ser Trp Thr Trp Arg Ser Leu Thr Leu Tyr Pro
    50                  55                  60

Ser Gln Pro Ser Asn Pro Leu Val Leu Glu Leu Gln Val His Leu Gly
65                  70                  75                  80

Asp Glu Gly Glu Phe Thr Cys Arg Ala Gln Asn Ser Leu Gly Ser Gln
                85                  90                  95

His Val Ser Leu Asn Leu Ser Leu Gln Gln Glu Tyr Thr Gly Lys Met
            100                 105                 110

Arg Pro Val Ser Gly Val Leu Leu
        115                 120

<210> SEQ ID NO 4
<211> LENGTH: 123
<212> TYPE: PRT
<213> ORGANISM: artificial sequence
<220> FEATURE:
<223> OTHER INFORMATION: Siglec-8 (236-336) spacer

<400> SEQUENCE: 4

Leu Asp Val Ser Tyr Pro Pro Trp Asn Leu Thr Met Thr Val Phe Gln
1               5                   10                  15

Gly Asp Ala Thr Ala Ser Thr Ala Leu Gly Asn Gly Ser Ser Leu Ser
            20                  25                  30

Val Leu Glu Gly Gln Ser Leu Arg Leu Val Cys Ala Val Asn Ser Asn
        35                  40                  45

Pro Pro Ala Arg Leu Ser Trp Thr Arg Gly Ser Leu Thr Leu Cys Pro
    50                  55                  60

Ser Arg Ser Ser Asn Pro Gly Leu Leu Glu Leu Pro Arg Val His Val
65                  70                  75                  80

Arg Asp Glu Gly Glu Phe Thr Cys Arg Ala Gln Asn Ala Gln Gly Ser
                85                  90                  95

Gln His Ile Ser Leu Ser Leu Ser Leu Gln Asn Glu Gly Thr Gly Thr
            100                 105                 110

Ser Arg Pro Val Ser Gln Val Thr Leu Ala Ala
        115                 120

<210> SEQ ID NO 5
<211> LENGTH: 245
<212> TYPE: PRT
<213> ORGANISM: artificial sequence
<220> FEATURE:
```

<223> OTHER INFORMATION: VH-(G4S)3 linker-VL of CD20 scFv

<400> SEQUENCE: 5

```
Gln Val Lys Leu Gln Glu Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Gln Gly Thr Thr Val Thr Val Ser Ser Gly Gly Gly Ser Gly
        115                 120                 125

Gly Gly Gly Ser Gly Gly Gly Ser Asp Ile Glu Leu Thr Gln Ser
    130                 135                 140

Pro Thr Ile Leu Ser Ala Ser Pro Gly Glu Lys Val Thr Met Thr Cys
145                 150                 155                 160

Arg Ala Ser Ser Val Asn Tyr Met Asp Trp Tyr Gln Lys Lys Pro
                165                 170                 175

Gly Ser Ser Pro Lys Pro Trp Ile Tyr Ala Thr Ser Asn Leu Ala Ser
            180                 185                 190

Gly Val Pro Ala Arg Phe Ser Gly Ser Gly Ser Gly Thr Ser Tyr Ser
        195                 200                 205

Leu Thr Ile Ser Arg Val Glu Ala Glu Asp Ala Ala Thr Tyr Tyr Cys
    210                 215                 220

Gln Gln Trp Ser Phe Asn Pro Pro Thr Phe Gly Gly Gly Thr Lys Leu
225                 230                 235                 240

Glu Ile Lys Ala Ser
                245
```

<210> SEQ ID NO 6
<211> LENGTH: 725
<212> TYPE: PRT
<213> ORGANISM: artificial sequence
<220> FEATURE:
<223> OTHER INFORMATION: Full CD20 Siglec-4 spacer CAR sequence

<400> SEQUENCE: 6

```
Met Asp Phe Gln Val Gln Ile Phe Ser Phe Leu Leu Ile Ser Ala Ser
1               5                   10                  15

Val Ile Met Ser Arg Met Ala Gln Val Lys Leu Gln Glu Ser Gly Ala
            20                  25                  30

Glu Leu Val Lys Pro Gly Ala Ser Val Lys Met Ser Cys Lys Ala Ser
        35                  40                  45

Gly Tyr Thr Phe Thr Ser Tyr Asn Met His Trp Val Lys Gln Thr Pro
    50                  55                  60

Gly Gln Gly Leu Glu Trp Ile Gly Ala Ile Tyr Pro Gly Asn Gly Asp
65                  70                  75                  80

Thr Ser Tyr Asn Gln Lys Phe Lys Gly Lys Ala Thr Leu Thr Ala Asp
                85                  90                  95
```

```
Lys Ser Ser Ser Thr Ala Tyr Met Gln Leu Ser Ser Leu Thr Ser Glu
        100                 105                 110

Asp Ser Ala Asp Tyr Tyr Cys Ala Arg Ser Asn Tyr Tyr Gly Ser Ser
            115                 120                 125

Tyr Trp Phe Phe Asp Val Trp Gly Gln Gly Thr Thr Val Thr Val Ser
    130                 135                 140

Ser Gly Gly Gly Ser Gly Gly Gly Ser Gly Gly Gly Gly Ser
145                 150                 155                 160

Asp Ile Glu Leu Thr Gln Ser Pro Thr Ile Leu Ser Ala Ser Pro Gly
                165                 170                 175

Glu Lys Val Thr Met Thr Cys Arg Ala Ser Ser Ser Val Asn Tyr Met
            180                 185                 190

Asp Trp Tyr Gln Lys Lys Pro Gly Ser Ser Pro Lys Pro Trp Ile Tyr
        195                 200                 205

Ala Thr Ser Asn Leu Ala Ser Gly Val Pro Ala Arg Phe Ser Gly Ser
    210                 215                 220

Gly Ser Gly Thr Ser Tyr Ser Leu Thr Ile Ser Arg Val Glu Ala Glu
225                 230                 235                 240

Asp Ala Ala Thr Tyr Tyr Cys Gln Gln Trp Ser Phe Asn Pro Pro Thr
                245                 250                 255

Phe Gly Gly Gly Thr Lys Leu Glu Ile Lys Ala Ser Tyr Pro Pro Val
            260                 265                 270

Ile Val Glu Met Asn Ser Ser Val Glu Ala Ile Glu Gly Ser His Val
        275                 280                 285

Ser Leu Leu Cys Gly Ala Asp Ser Asn Pro Pro Leu Leu Thr Trp
    290                 295                 300

Met Arg Asp Gly Thr Val Leu Arg Glu Ala Val Ala Glu Ser Leu Leu
305                 310                 315                 320

Leu Glu Leu Glu Glu Val Thr Pro Ala Glu Asp Gly Val Tyr Ala Cys
                325                 330                 335

Leu Ala Glu Asn Ala Tyr Gly Gln Asp Asn Arg Thr Val Gly Leu Ser
            340                 345                 350

Val Met Tyr Ala Pro Trp Lys Pro Thr Val Asn Gly Thr Met Val Ala
        355                 360                 365

Val Glu Gly Glu Thr Val Ser Ile Leu Cys Ser Thr Gln Ser Asn Pro
370                 375                 380

Asp Pro Ile Leu Thr Ile Phe Lys Glu Lys Gln Ile Leu Ser Thr Val
385                 390                 395                 400

Ile Tyr Glu Ser Glu Leu Gln Leu Glu Leu Pro Ala Val Ser Pro Glu
                405                 410                 415

Asp Asp Gly Glu Tyr Trp Cys Val Ala Glu Asn Gln Tyr Gly Gln Arg
            420                 425                 430

Ala Thr Ala Phe Asn Leu Ser Val Glu Phe Ala Pro Val Leu Leu Leu
        435                 440                 445

Glu Ser His Cys Ala Ala Ala Arg Asp Thr Val Gln Cys Leu Cys Val
    450                 455                 460

Val Lys Ser Asn Pro Glu Pro Ser Val Ala Phe Glu Leu Pro Ser Arg
465                 470                 475                 480

Asn Val Thr Val Asn Glu Ser Glu Arg Glu Phe Val Tyr Ser Glu Arg
                485                 490                 495

Ser Gly Leu Val Leu Thr Ser Ile Leu Thr Leu Arg Gly Gln Ala Gln
            500                 505                 510
```

```
Ala Pro Pro Arg Val Ile Cys Thr Ala Arg Asn Leu Tyr Gly Ala Lys
            515                 520                 525

Ser Leu Glu Leu Pro Phe Gln Gly Ala His Arg Leu Met Trp Ala Lys
        530                 535                 540

Ile Gly Pro Ile Tyr Ile Trp Ala Pro Leu Ala Gly Thr Cys Gly Val
545                 550                 555                 560

Leu Leu Leu Ser Leu Val Ile Thr Leu Tyr Cys Lys Arg Gly Arg Lys
                565                 570                 575

Lys Leu Leu Tyr Ile Phe Lys Gln Pro Phe Met Arg Pro Val Gln Thr
            580                 585                 590

Thr Gln Glu Glu Asp Gly Cys Ser Cys Arg Phe Pro Glu Glu Glu Glu
        595                 600                 605

Gly Gly Cys Glu Leu Arg Val Lys Phe Ser Arg Ser Ala Asp Ala Pro
    610                 615                 620

Ala Tyr Gln Gln Gly Gln Asn Gln Leu Tyr Asn Glu Leu Asn Leu Gly
625                 630                 635                 640

Arg Arg Glu Glu Tyr Asp Val Leu Asp Lys Arg Arg Gly Arg Asp Pro
                645                 650                 655

Glu Met Gly Gly Lys Pro Arg Arg Lys Asn Pro Gln Glu Gly Leu Tyr
            660                 665                 670

Asn Glu Leu Gln Lys Asp Lys Met Ala Glu Ala Tyr Ser Glu Ile Gly
        675                 680                 685

Met Lys Gly Glu Arg Arg Arg Gly Lys Gly His Asp Gly Leu Tyr Gln
    690                 695                 700

Gly Leu Ser Thr Ala Thr Lys Asp Thr Tyr Asp Ala Leu His Met Gln
705                 710                 715                 720

Ala Leu Pro Pro Arg
                725

<210> SEQ ID NO 7
<211> LENGTH: 650
<212> TYPE: PRT
<213> ORGANISM: artificial sequence
<220> FEATURE:
<223> OTHER INFORMATION: Full CD20 Siglec-7.1 spacer CAR sequence

<400> SEQUENCE: 7

Met Asp Phe Gln Val Gln Ile Phe Ser Phe Leu Leu Ile Ser Ala Ser
1               5                   10                  15

Val Ile Met Ser Arg Met Ala Gln Val Lys Leu Gln Glu Ser Gly Ala
            20                  25                  30

Glu Leu Val Lys Pro Gly Ala Ser Val Lys Met Ser Cys Lys Ala Ser
        35                  40                  45

Gly Tyr Thr Phe Thr Ser Tyr Asn Met His Trp Val Lys Gln Thr Pro
    50                  55                  60

Gly Gln Gly Leu Glu Trp Ile Gly Ala Ile Tyr Pro Gly Asn Gly Asp
65                  70                  75                  80

Thr Ser Tyr Asn Gln Lys Phe Lys Gly Lys Ala Thr Leu Thr Ala Asp
                85                  90                  95

Lys Ser Ser Ser Thr Ala Tyr Met Gln Leu Ser Ser Leu Thr Ser Glu
            100                 105                 110

Asp Ser Ala Asp Tyr Tyr Cys Ala Arg Ser Asn Tyr Tyr Gly Ser Ser
        115                 120                 125

Tyr Trp Phe Phe Asp Val Trp Gly Gln Gly Thr Thr Val Thr Val Ser
    130                 135                 140
```

```
Ser Gly Gly Gly Gly Ser Gly Gly Gly Ser Gly Gly Gly Ser
145                 150                 155                 160

Asp Ile Glu Leu Thr Gln Ser Pro Thr Ile Leu Ser Ala Ser Pro Gly
            165                 170                 175

Glu Lys Val Thr Met Thr Cys Arg Ala Ser Ser Ser Val Asn Tyr Met
            180                 185                 190

Asp Trp Tyr Gln Lys Lys Pro Gly Ser Ser Pro Lys Pro Trp Ile Tyr
        195                 200                 205

Ala Thr Ser Asn Leu Ala Ser Gly Val Pro Ala Arg Phe Ser Gly Ser
        210                 215                 220

Gly Ser Gly Thr Ser Tyr Ser Leu Thr Ile Ser Arg Val Glu Ala Glu
225                 230                 235                 240

Asp Ala Ala Thr Tyr Tyr Cys Gln Gln Trp Ser Phe Asn Pro Pro Thr
            245                 250                 255

Phe Gly Gly Gly Thr Lys Leu Glu Ile Lys Ala Ser Pro Asn Ile Leu
            260                 265                 270

Ile Pro Gly Thr Leu Glu Ser Gly Cys Phe Gln Asn Leu Thr Cys Ser
        275                 280                 285

Val Pro Trp Ala Cys Glu Gln Gly Thr Pro Pro Met Ile Ser Trp Met
290                 295                 300

Gly Thr Ser Val Ser Pro Leu His Pro Ser Thr Thr Arg Ser Ser Val
305                 310                 315                 320

Leu Thr Leu Ile Pro Gln Pro Gln His His Gly Thr Ser Leu Thr Cys
            325                 330                 335

Gln Val Thr Leu Pro Gly Ala Gly Val Thr Thr Asn Arg Thr Ile Gln
            340                 345                 350

Leu Asn Val Ser Tyr Pro Pro Gln Asn Leu Thr Val Thr Val Phe Gln
        355                 360                 365

Gly Glu Gly Thr Ala Ser Thr Ala Leu Gly Asn Ser Ser Ser Leu Ser
        370                 375                 380

Val Leu Glu Gly Gln Ser Leu Arg Leu Val Cys Ala Val Asp Ser Asn
385                 390                 395                 400

Pro Pro Ala Arg Leu Ser Trp Thr Trp Arg Ser Leu Thr Leu Tyr Pro
            405                 410                 415

Ser Gln Pro Ser Asn Pro Leu Val Leu Glu Leu Gln Val His Leu Gly
            420                 425                 430

Asp Glu Gly Glu Phe Thr Cys Arg Ala Gln Asn Ser Leu Gly Ser Gln
        435                 440                 445

His Val Ser Leu Asn Leu Ser Leu Gln Gln Glu Tyr Thr Gly Lys Met
        450                 455                 460

Arg Pro Val Ser Gly Val Leu Leu Ile Tyr Ile Trp Ala Pro Leu Ala
465                 470                 475                 480

Gly Thr Cys Gly Val Leu Leu Leu Ser Leu Val Ile Thr Leu Tyr Cys
            485                 490                 495

Lys Arg Gly Arg Lys Lys Leu Leu Tyr Ile Phe Lys Gln Pro Phe Met
            500                 505                 510

Arg Pro Val Gln Thr Thr Gln Glu Glu Asp Gly Cys Ser Cys Arg Phe
        515                 520                 525

Pro Glu Glu Glu Glu Gly Gly Cys Glu Leu Arg Val Lys Phe Ser Arg
        530                 535                 540

Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
```

```
                        565                 570                 575
Arg Gly Arg Asp Pro Glu Met Gly Gly Lys Pro Arg Arg Lys Asn Pro
                580                 585                 590

Gln Glu Gly Leu Tyr Asn Glu Leu Gln Lys Asp Lys Met Ala Glu Ala
            595                 600                 605

Tyr Ser Glu Ile Gly Met Lys Gly Glu Arg Arg Arg Gly Lys Gly His
        610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
                645                 650

<210> SEQ ID NO 8
<211> LENGTH: 566
<212> TYPE: PRT
<213> ORGANISM: artificial sequence
<220> FEATURE:
<223> OTHER INFORMATION: Full CD20 Siglec-7.2 spacer CAR sequence

<400> SEQUENCE: 8

Met Asp Phe Gln Val Gln Ile Phe Ser Phe Leu Leu Ile Ser Ala Ser
1               5                   10                  15

Val Ile Met Ser Arg Met Ala Gln Val Lys Leu Gln Glu Ser Gly Ala
            20                  25                  30

Glu Leu Val Lys Pro Gly Ala Ser Val Lys Met Ser Cys Lys Ala Ser
        35                  40                  45

Gly Tyr Thr Phe Thr Ser Tyr Asn Met His Trp Val Lys Gln Thr Pro
    50                  55                  60

Gly Gln Gly Leu Glu Trp Ile Gly Ala Ile Tyr Pro Gly Asn Gly Asp
65                  70                  75                  80

Thr Ser Tyr Asn Gln Lys Phe Lys Gly Lys Ala Thr Leu Thr Ala Asp
                85                  90                  95

Lys Ser Ser Ser Thr Ala Tyr Met Gln Leu Ser Ser Leu Thr Ser Glu
            100                 105                 110

Asp Ser Ala Asp Tyr Tyr Cys Ala Arg Ser Asn Tyr Tyr Gly Ser Ser
        115                 120                 125

Tyr Trp Phe Phe Asp Val Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Glu Leu Thr Gln Ser Pro Thr Ile Leu Ser Ala Ser Pro Gly
                165                 170                 175

Glu Lys Val Thr Met Thr Cys Arg Ala Ser Ser Ser Val Asn Tyr Met
            180                 185                 190

Asp Trp Tyr Gln Lys Lys Pro Gly Ser Ser Pro Lys Pro Trp Ile Tyr
        195                 200                 205

Ala Thr Ser Asn Leu Ala Ser Gly Val Pro Ala Arg Phe Ser Gly Ser
    210                 215                 220

Gly Ser Gly Thr Ser Tyr Ser Leu Thr Ile Ser Arg Val Glu Ala Glu
225                 230                 235                 240

Asp Ala Ala Thr Tyr Tyr Cys Gln Gln Trp Ser Phe Asn Pro Pro Thr
                245                 250                 255

Phe Gly Gly Gly Thr Lys Leu Glu Ile Lys Ala Ser Leu Asn Val Ser
            260                 265                 270

Tyr Pro Pro Gln Asn Leu Thr Val Thr Val Phe Gln Gly Glu Gly Thr
```

```
            275                 280                 285
Ala Ser Thr Ala Leu Gly Asn Ser Ser Leu Ser Val Leu Glu Gly
    290                 295                 300

Gln Ser Leu Arg Leu Val Cys Ala Val Asp Ser Asn Pro Ala Arg
305                 310                 315                 320

Leu Ser Trp Thr Trp Arg Ser Leu Thr Leu Tyr Pro Ser Gln Pro Ser
                325                 330                 335

Asn Pro Leu Val Leu Glu Leu Gln Val His Leu Gly Asp Glu Gly Glu
                340                 345                 350

Phe Thr Cys Arg Ala Gln Asn Ser Leu Gly Ser Gln His Val Ser Leu
                355                 360                 365

Asn Leu Ser Leu Gln Gln Glu Tyr Thr Gly Lys Met Arg Pro Val Ser
    370                 375                 380

Gly Val Leu Leu Ile Tyr Ile Trp Ala Pro Leu Ala Gly Thr Cys Gly
385                 390                 395                 400

Val Leu Leu Leu Ser Leu Val Ile Thr Leu Tyr Cys Lys Arg Gly Arg
                405                 410                 415

Lys Lys Leu Leu Tyr Ile Phe Lys Gln Pro Phe Met Arg Pro Val Gln
                420                 425                 430

Thr Thr Gln Glu Glu Asp Gly Cys Ser Cys Arg Phe Pro Glu Glu Glu
                435                 440                 445

Glu Gly Gly Cys Glu Leu Arg Val Lys Phe Ser Arg Ser Ala Asp Ala
    450                 455                 460

Pro Ala Tyr Gln Gln Gly Gln Asn Gln Leu Tyr Asn Glu Leu Asn Leu
465                 470                 475                 480

Gly Arg Arg Glu Glu Tyr Asp Val Leu Asp Lys Arg Arg Gly Arg Asp
                485                 490                 495

Pro Glu Met Gly Gly Lys Pro Arg Arg Lys Asn Pro Gln Glu Gly Leu
                500                 505                 510

Tyr Asn Glu Leu Gln Lys Asp Lys Met Ala Glu Ala Tyr Ser Glu Ile
                515                 520                 525

Gly Met Lys Gly Glu Arg Arg Arg Gly Lys Gly His Asp Gly Leu Tyr
    530                 535                 540

Gln Gly Leu Ser Thr Ala Thr Lys Asp Thr Tyr Asp Ala Leu His Met
545                 550                 555                 560

Gln Ala Leu Pro Pro Arg
                565

<210> SEQ ID NO 9
<211> LENGTH: 569
<212> TYPE: PRT
<213> ORGANISM: artificial sequence
<220> FEATURE:
<223> OTHER INFORMATION: Full CD20 Siglec-8 spacer CAR sequence

<400> SEQUENCE: 9

Met Asp Phe Gln Val Gln Ile Phe Ser Phe Leu Leu Ile Ser Ala Ser
1               5                   10                  15

Val Ile Met Ser Arg Met Ala Gln Val Lys Leu Gln Glu Ser Gly Ala
                20                  25                  30

Glu Leu Val Lys Pro Gly Ala Ser Val Lys Met Ser Cys Lys Ala Ser
                35                  40                  45

Gly Tyr Thr Phe Thr Ser Tyr Asn Met His Trp Val Lys Gln Thr Pro
                50                  55                  60

Gly Gln Gly Leu Glu Trp Ile Gly Ala Ile Tyr Pro Gly Asn Gly Asp
```

-continued

```
            65                  70                  75                  80
Thr Ser Tyr Asn Gln Lys Phe Lys Gly Lys Ala Thr Leu Thr Ala Asp
                85                  90                  95
Lys Ser Ser Ser Thr Ala Tyr Met Gln Leu Ser Ser Leu Thr Ser Glu
            100                 105                 110
Asp Ser Ala Asp Tyr Tyr Cys Ala Arg Ser Asn Tyr Tyr Gly Ser Ser
            115                 120                 125
Tyr Trp Phe Phe Asp Val Trp Gly Gln Gly Thr Thr Val Thr Val Ser
            130                 135                 140
Ser Gly Gly Gly Gly Ser Gly Gly Gly Gly Ser Gly Gly Gly Gly Ser
145                 150                 155                 160
Asp Ile Glu Leu Thr Gln Ser Pro Thr Ile Leu Ser Ala Ser Pro Gly
                165                 170                 175
Glu Lys Val Thr Met Thr Cys Arg Ala Ser Ser Ser Val Asn Tyr Met
            180                 185                 190
Asp Trp Tyr Gln Lys Lys Pro Gly Ser Ser Pro Lys Pro Trp Ile Tyr
            195                 200                 205
Ala Thr Ser Asn Leu Ala Ser Gly Val Pro Ala Arg Phe Ser Gly Ser
            210                 215                 220
Gly Ser Gly Thr Ser Tyr Ser Leu Thr Ile Ser Arg Val Glu Ala Glu
225                 230                 235                 240
Asp Ala Ala Thr Tyr Tyr Cys Gln Gln Trp Ser Phe Asn Pro Pro Thr
            245                 250                 255
Phe Gly Gly Gly Thr Lys Leu Glu Ile Lys Ala Ser Leu Asp Val Ser
            260                 265                 270
Tyr Pro Pro Trp Asn Leu Thr Met Thr Val Phe Gln Gly Asp Ala Thr
            275                 280                 285
Ala Ser Thr Ala Leu Gly Asn Gly Ser Ser Leu Ser Val Leu Glu Gly
            290                 295                 300
Gln Ser Leu Arg Leu Val Cys Ala Val Asn Ser Asn Pro Pro Ala Arg
305                 310                 315                 320
Leu Ser Trp Thr Arg Gly Ser Leu Thr Leu Cys Pro Ser Arg Ser Ser
                325                 330                 335
Asn Pro Gly Leu Leu Glu Leu Pro Arg Val His Val Arg Asp Glu Gly
            340                 345                 350
Glu Phe Thr Cys Arg Ala Gln Asn Ala Gln Gly Ser Gln His Ile Ser
            355                 360                 365
Leu Ser Leu Ser Leu Gln Asn Glu Gly Thr Gly Thr Ser Arg Pro Val
            370                 375                 380
Ser Gln Val Thr Leu Ala Ala Ile Tyr Ile Trp Ala Pro Leu Ala Gly
385                 390                 395                 400
Thr Cys Gly Val Leu Leu Leu Ser Leu Val Ile Thr Leu Tyr Cys Lys
                405                 410                 415
Arg Gly Arg Lys Lys Leu Leu Tyr Ile Phe Lys Gln Pro Phe Met Arg
            420                 425                 430
Pro Val Gln Thr Thr Gln Glu Glu Asp Gly Cys Ser Cys Arg Phe Pro
            435                 440                 445
Glu Glu Glu Glu Gly Gly Cys Glu Leu Arg Val Lys Phe Ser Arg Ser
            450                 455                 460
Ala Asp Ala Pro Ala Tyr Gln Gln Gly Gln Asn Gln Leu Tyr Asn Glu
465                 470                 475                 480
Leu Asn Leu Gly Arg Arg Glu Glu Tyr Asp Val Leu Asp Lys Arg Arg
                485                 490                 495
```

Gly Arg Asp Pro Glu Met Gly Lys Pro Arg Arg Lys Asn Pro Gln
            500                 505                 510

Glu Gly Leu Tyr Asn Glu Leu Gln Lys Asp Lys Met Ala Glu Ala Tyr
            515                 520                 525

Ser Glu Ile Gly Met Lys Gly Glu Arg Arg Arg Gly Lys Gly His Asp
530                 535                 540

Gly Leu Tyr Gln Gly Leu Ser Thr Ala Thr Lys Asp Thr Tyr Asp Ala
545                 550                 555                 560

Leu His Met Gln Ala Leu Pro Pro Arg
                565

<210> SEQ ID NO 10
<211> LENGTH: 245
<212> TYPE: PRT
<213> ORGANISM: artificial sequence
<220> FEATURE:
<223> OTHER INFORMATION: TSPAN8 scFv

<400> SEQUENCE: 10

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Phe Ile Arg Asn Lys Ala Ser Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Ala His Ser Tyr Tyr Gly Tyr Asp Tyr Phe Asp Tyr
            100                 105                 110

Trp Gly Gln Gly Val Met Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ala Ser Leu Ser Ala Ser Leu Glu Glu Ile Val Thr Ile Thr
145                 150                 155                 160

Cys Gln Ala Ser Gln Asp Ile Gly Asn Trp Leu Ser Trp Tyr Gln Gln
                165                 170                 175

Lys Pro Gly Lys Ser Pro Gln Leu Leu Ile Tyr Gly Ala Thr Ser Leu
            180                 185                 190

Ala Asp Gly Val Pro Ser Arg Phe Ser Gly Ser Arg Ser Gly Thr Gln
        195                 200                 205

Tyr Ser Leu Lys Ile Ser Arg Leu Gln Val Glu Asp Ile Arg Ile Tyr
    210                 215                 220

Tyr Cys Leu Gln Ala Tyr Ser Ala Pro Trp Thr Phe Gly Gly Gly Thr
225                 230                 235                 240

Lys Leu Glu Leu Lys
                245

<210> SEQ ID NO 11
<211> LENGTH: 726
<212> TYPE: PRT
<213> ORGANISM: artificial sequence
<220> FEATURE:
<223> OTHER INFORMATION: Full TSPAN8 Siglec-4 spacer CAR sequence

<400> SEQUENCE: 11

```
Met Ala Leu Pro Val Thr Ala Leu Leu Leu Pro Leu Ala Leu Leu Leu
1               5                   10                  15

His Ala Ala Arg Pro Glu Val Lys Leu Leu Glu Ser Gly Gly Gly Leu
            20                  25                  30

Val Gln Pro Gly Gly Ser Met Arg Leu Ser Cys Ala Ala Ser Gly Phe
        35                  40                  45

Thr Phe Thr Asp Phe Tyr Met Asn Trp Ile Arg Gln Pro Ala Gly Lys
    50                  55                  60

Ala Pro Glu Trp Leu Gly Phe Ile Arg Asn Lys Ala Ser Gly Tyr Thr
65                  70                  75                  80

Thr Glu Tyr Asn Pro Ser Val Lys Gly Arg Phe Thr Ile Ser Arg Asp
                85                  90                  95

Asn Thr Gln Asn Met Leu Tyr Leu Gln Met Asn Thr Leu Arg Ala Glu
            100                 105                 110

Asp Thr Ala Thr Tyr Tyr Cys Ala Arg Ala His Ser Tyr Tyr Gly Tyr
        115                 120                 125

Asp Tyr Phe Asp Tyr Trp Gly Gln Gly Val Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ala Ser Leu Ser Ala Ser Leu Glu Glu
                165                 170                 175

Ile Val Thr Ile Thr Cys Gln Ala Ser Gln Asp Ile Gly Asn Trp Leu
            180                 185                 190

Ser Trp Tyr Gln Gln Lys Pro Gly Lys Ser Pro Gln Leu Leu Ile Tyr
        195                 200                 205

Gly Ala Thr Ser Leu Ala Asp Gly Val Pro Ser Arg Phe Ser Gly Ser
    210                 215                 220

Arg Ser Gly Thr Gln Tyr Ser Leu Lys Ile Ser Arg Leu Gln Val Glu
225                 230                 235                 240

Asp Ile Arg Ile Tyr Tyr Cys Leu Gln Ala Tyr Ser Ala Pro Trp Thr
                245                 250                 255

Phe Gly Gly Gly Thr Lys Leu Glu Leu Lys Ala Ala Ser Tyr Pro Pro
            260                 265                 270

Val Ile Val Glu Met Asn Ser Ser Val Glu Ala Ile Glu Gly Ser His
        275                 280                 285

Val Ser Leu Leu Cys Gly Ala Asp Ser Asn Pro Pro Pro Leu Leu Thr
    290                 295                 300

Trp Met Arg Asp Gly Thr Val Leu Arg Glu Ala Val Ala Glu Ser Leu
305                 310                 315                 320

Leu Leu Glu Leu Glu Glu Val Thr Pro Ala Glu Asp Gly Val Tyr Ala
                325                 330                 335

Cys Leu Ala Glu Asn Ala Tyr Gly Gln Asp Asn Arg Thr Val Gly Leu
            340                 345                 350

Ser Val Met Tyr Ala Pro Trp Lys Pro Thr Val Asn Gly Thr Met Val
        355                 360                 365

Ala Val Glu Gly Glu Thr Val Ser Ile Leu Cys Ser Thr Gln Ser Asn
    370                 375                 380

Pro Asp Pro Ile Leu Thr Ile Phe Lys Glu Lys Gln Ile Leu Ser Thr
385                 390                 395                 400
```

-continued

```
Val Ile Tyr Glu Ser Glu Leu Gln Leu Glu Leu Pro Ala Val Ser Pro
            405                 410                 415
Glu Asp Asp Gly Glu Tyr Trp Cys Val Ala Glu Asn Gln Tyr Gly Gln
        420                 425                 430
Arg Ala Thr Ala Phe Asn Leu Ser Val Glu Phe Ala Pro Val Leu Leu
    435                 440                 445
Leu Glu Ser His Cys Ala Ala Arg Asp Thr Val Gln Cys Leu Cys
450                 455                 460
Val Val Lys Ser Asn Pro Glu Pro Ser Val Ala Phe Glu Leu Pro Ser
465                 470                 475                 480
Arg Asn Val Thr Val Asn Glu Ser Glu Arg Glu Phe Val Tyr Ser Glu
                485                 490                 495
Arg Ser Gly Leu Val Leu Thr Ser Ile Leu Thr Leu Arg Gly Gln Ala
            500                 505                 510
Gln Ala Pro Pro Arg Val Ile Cys Thr Ala Arg Asn Leu Tyr Gly Ala
        515                 520                 525
Lys Ser Leu Glu Leu Pro Phe Gln Gly Ala His Arg Leu Met Trp Ala
    530                 535                 540
Lys Ile Gly Pro Ile Tyr Ile Trp Ala Pro Leu Ala Gly Thr Cys Gly
545                 550                 555                 560
Val Leu Leu Leu Ser Leu Val Ile Thr Leu Tyr Cys Lys Arg Gly Arg
                565                 570                 575
Lys Lys Leu Leu Tyr Ile Phe Lys Gln Pro Phe Met Arg Pro Val Gln
            580                 585                 590
Thr Thr Gln Glu Glu Asp Gly Cys Ser Cys Arg Phe Pro Glu Glu Glu
        595                 600                 605
Glu Gly Gly Cys Glu Leu Arg Val Lys Phe Ser Arg Ser Ala Asp Ala
    610                 615                 620
Pro Ala Tyr Gln Gln Gly Gln Asn Gln Leu Tyr Asn Glu Leu Asn Leu
625                 630                 635                 640
Gly Arg Arg Glu Glu Tyr Asp Val Leu Asp Lys Arg Gly Arg Asp
                645                 650                 655
Pro Glu Met Gly Gly Lys Pro Arg Arg Lys Asn Pro Gln Glu Gly Leu
            660                 665                 670
Tyr Asn Glu Leu Gln Lys Asp Lys Met Ala Glu Ala Tyr Ser Glu Ile
        675                 680                 685
Gly Met Lys Gly Glu Arg Arg Arg Gly Lys Gly His Asp Gly Leu Tyr
    690                 695                 700
Gln Gly Leu Ser Thr Ala Thr Lys Asp Thr Tyr Asp Ala Leu His Met
705                 710                 715                 720
Gln Ala Leu Pro Pro Arg
                725
```

<210> SEQ ID NO 12
<211> LENGTH: 115
<212> TYPE: PRT
<213> ORGANISM: artificial sequence
<220> FEATURE:
<223> OTHER INFORMATION: Siglec-3 (145-228; C169S) spacer

<400> SEQUENCE: 12

```
Pro Lys Ile Leu Ile Pro Gly Thr Leu Glu Pro Gly His Ser Lys Asn
1               5                   10                  15
Leu Thr Cys Ser Val Ser Trp Ala Ser Glu Gln Gly Thr Pro Pro Ile
            20                  25                  30
```

```
Phe Ser Trp Leu Ser Ala Ala Pro Thr Ser Leu Gly Pro Arg Thr Thr
        35                  40                  45

His Ser Ser Val Leu Ile Ile Thr Pro Arg Pro Gln Asp His Gly Thr
 50                  55                  60

Asn Leu Thr Cys Gln Val Lys Phe Ala Gly Ala Gly Val Thr Thr Glu
 65                  70                  75                  80

Arg Thr Ile Gln Leu Asn Val Thr Tyr Val Pro Gln Asn Pro Thr Thr
                 85                  90                  95

Gly Ile Phe Pro Gly Asp Gly Ser Gly Lys Gln Glu Thr Arg Ala Gly
                100                 105                 110

Val Val His
        115
```

<210> SEQ ID NO 13
<211> LENGTH: 561
<212> TYPE: PRT
<213> ORGANISM: artificial sequence
<220> FEATURE:
<223> OTHER INFORMATION: Full CD20 Siglec-3 spacer CAR sequence

<400> SEQUENCE: 13

```
Met Asp Phe Gln Val Gln Ile Phe Ser Phe Leu Leu Ile Ser Ala Ser
 1               5                  10                  15

Val Ile Met Ser Arg Met Ala Gln Val Lys Leu Gln Glu Ser Gly Ala
                 20                  25                  30

Glu Leu Val Lys Pro Gly Ala Ser Val Lys Met Ser Cys Lys Ala Ser
             35                  40                  45

Gly Tyr Thr Phe Thr Ser Tyr Asn Met His Trp Val Lys Gln Thr Pro
 50                  55                  60

Gly Gln Gly Leu Glu Trp Ile Gly Ala Ile Tyr Pro Gly Asn Gly Asp
 65                  70                  75                  80

Thr Ser Tyr Asn Gln Lys Phe Lys Gly Lys Ala Thr Leu Thr Ala Asp
                 85                  90                  95

Lys Ser Ser Ser Thr Ala Tyr Met Gln Leu Ser Ser Leu Thr Ser Glu
                100                 105                 110

Asp Ser Ala Asp Tyr Tyr Cys Ala Arg Ser Asn Tyr Tyr Gly Ser Ser
             115                 120                 125

Tyr Trp Phe Phe Asp Val Trp Gly Gln Gly Thr Thr Val Thr Val Ser
        130                 135                 140

Ser Gly Gly Gly Gly Ser Gly Gly Gly Gly Ser Gly Gly Gly Gly Ser
145                 150                 155                 160

Asp Ile Glu Leu Thr Gln Ser Pro Thr Ile Leu Ser Ala Ser Pro Gly
                165                 170                 175

Glu Lys Val Thr Met Thr Cys Arg Ala Ser Ser Ser Val Asn Tyr Met
             180                 185                 190

Asp Trp Tyr Gln Lys Lys Pro Gly Ser Ser Pro Lys Pro Trp Ile Tyr
        195                 200                 205

Ala Thr Ser Asn Leu Ala Ser Gly Val Pro Ala Arg Phe Ser Gly Ser
 210                 215                 220

Gly Ser Gly Thr Ser Tyr Ser Leu Thr Ile Ser Arg Val Glu Ala Glu
225                 230                 235                 240

Asp Ala Ala Thr Tyr Tyr Cys Gln Gln Trp Ser Phe Asn Pro Pro Thr
                245                 250                 255

Phe Gly Gly Gly Thr Lys Leu Glu Ile Lys Ala Ser Pro Lys Ile Leu
             260                 265                 270
```

```
Ile Pro Gly Thr Leu Glu Pro Gly His Ser Lys Asn Leu Thr Cys Ser
        275                 280                 285
Val Ser Trp Ala Ser Glu Gln Gly Thr Pro Pro Ile Phe Ser Trp Leu
        290                 295                 300
Ser Ala Ala Pro Thr Ser Leu Gly Pro Arg Thr Thr His Ser Ser Val
305                 310                 315                 320
Leu Ile Ile Thr Pro Arg Pro Gln Asp His Gly Thr Asn Leu Thr Cys
                325                 330                 335
Gln Val Lys Phe Ala Gly Ala Gly Val Thr Thr Glu Arg Thr Ile Gln
                340                 345                 350
Leu Asn Val Thr Tyr Val Pro Gln Asn Pro Thr Thr Gly Ile Phe Pro
                355                 360                 365
Gly Asp Gly Ser Gly Lys Gln Glu Thr Arg Ala Gly Val Val His Ile
        370                 375                 380
Tyr Ile Trp Ala Pro Leu Ala Gly Thr Cys Gly Val Leu Leu Leu Ser
385                 390                 395                 400
Leu Val Ile Thr Leu Tyr Cys Lys Arg Gly Arg Lys Lys Leu Leu Tyr
                405                 410                 415
Ile Phe Lys Gln Pro Phe Met Arg Pro Val Gln Thr Thr Gln Glu Glu
                420                 425                 430
Asp Gly Cys Ser Cys Arg Phe Pro Glu Glu Glu Glu Gly Gly Cys Glu
                435                 440                 445
Leu Arg Val Lys Phe Ser Arg Ser Ala Asp Ala Pro Ala Tyr Gln Gln
        450                 455                 460
Gly Gln Asn Gln Leu Tyr Asn Glu Leu Asn Leu Gly Arg Arg Glu Glu
465                 470                 475                 480
Tyr Asp Val Leu Asp Lys Arg Arg Gly Arg Asp Pro Glu Met Gly Gly
                485                 490                 495
Lys Pro Arg Arg Lys Asn Pro Gln Glu Gly Leu Tyr Asn Glu Leu Gln
                500                 505                 510
Lys Asp Lys Met Ala Glu Ala Tyr Ser Glu Ile Gly Met Lys Gly Glu
        515                 520                 525
Arg Arg Arg Gly Lys Gly His Asp Gly Leu Tyr Gln Gly Leu Ser Thr
        530                 535                 540
Ala Thr Lys Asp Thr Tyr Asp Ala Leu His Met Gln Ala Leu Pro Pro
545                 550                 555                 560
Arg
```